US00RE36914E

United States Patent [19]

Carlsen et al.

[11] E Patent Number: Re. 36,914

[45] Reissued Date of Patent: Oct. 17, 2000

[54] DIALYSATE FILTER INCLUDING AN ASYMMETRIC MICROPOROUS, HOLLOW FIBER MEMBRANE INCORPORATING A POLYIMIDE

[76] Inventors: Daniel B. Carlsen, 3410 W. Via Montoya Dr., Phoenix, Ariz. 85027-1661; Robert G. Andrus, 15300 37th Ave. North, Apt. B 220, Plymouth, Minn. 55446; Robert T. Hall, II, 20175 Rhoda Ave., Welch, Minn. 55089

[21] Appl. No.: 09/250,449

[22] Filed: Feb. 16, 1999

Related U.S. Patent Documents

Reissue of:

[64] Patent No.: 5,605,627
Issued: Feb. 25, 1997
Appl. No.: 08/418,802
Filed: Apr. 7, 1995

U.S. Applications:

[63] Continuation-in-part of application No. 08/058,904, May 6, 1993, Pat. No. 5,762,798, which is a continuation-in-part of application No. 07/958,027, Oct. 7, 1992, abandoned.

[51] Int. Cl.[7] ..... B01D 63/00

[52] U.S. Cl. ..... 210/321.79; 210/321.8; 210/321.71; 210/321.89; 210/500.23; 210/500.39; 210/500.37; 210/257.2

[58] Field of Search ..... 210/321.6, 321.79, 210/321.71, 321.8, 645, 500.23, 500.37, 500.39, 321.65, 321.89

[56] References Cited

U.S. PATENT DOCUMENTS

| | | |
|---|---|---|
| 3,180,845 | 4/1965 | Knudsen . |
| 3,423,491 | 1/1969 | McLain et al. . |
| 3,526,588 | 9/1970 | Michaels et al. . |
| 3,615,024 | 10/1971 | Michaels . |
| 3,691,068 | 9/1972 | Cross . |
| 3,708,458 | 1/1973 | Alberino et al. . |
| 3,763,055 | 10/1973 | White et al. . |

(List continued on next page.)

FOREIGN PATENT DOCUMENTS

| | | |
|---|---|---|
| 0082433 | 6/1983 | European Pat. Off. . |
| 0125908 | 11/1984 | European Pat. Off. . |
| 0422885 | 4/1991 | European Pat. Off. . |
| 0446947 | 9/1991 | European Pat. Off. . |
| 0456143 | 11/1991 | European Pat. Off. . |
| 0488018 | 6/1992 | European Pat. Off. . |
| 2482468 | 11/1981 | France . |
| 2829630 | 1/1974 | Germany . |
| 2651818 | 6/1977 | Germany . |
| 3018667 | 11/1981 | Germany . |
| 3149976 | 6/1983 | Germany . |
| 59-230604 | 12/1984 | Japan . |
| 3-178324 | 12/1987 | Japan . |
| 3-270721 | 12/1991 | Japan . |
| 4-227831 | 8/1992 | Japan . |
| 4-267934 | 9/1992 | Japan . |
| 8702924 | 12/1987 | Netherlands . |
| 2102333 | 2/1983 | United Kingdom . |

OTHER PUBLICATIONS

C. Dinarello, "Cytokines: Agents Provocateurs in Hemodialysis?", Kidney International, vol. 41 (1992), pp. 683–694.

"Quality Assurance for the '90s: A Bicarbonate Dialysate Monography", Special Supp. to Neph. News & Issues, Jan. 1992.

(List continued on next page.)

*Primary Examiner*—Ana Fortuna
*Attorney, Agent, or Firm*—Barbara A. Wrigley

[57] ABSTRACT

A dialysate filter including asymmetric, microporous, hollow fiber membranes incorporating a polyimide. The dialysate filter connects to the dialysis machine immediately before the dialyzer ensuring complete filtration of the dialysate, easy visual inspection, quick installation and removal, and easy disinfection of the filter.

30 Claims, 9 Drawing Sheets

U.S. PATENT DOCUMENTS

| | | |
|---|---|---|
| 3,775,308 | 11/1973 | Yasuda . |
| 3,948,823 | 4/1976 | Lee et al. . |
| 4,026,977 | 5/1977 | Bourganel . |
| 4,046,843 | 9/1977 | Sano et al. . |
| 4,051,300 | 9/1977 | Klein et al. . |
| 4,079,007 | 3/1978 | Hutchisson . |
| 4,100,238 | 7/1978 | Shinomura . |
| 4,113,628 | 9/1978 | Alegranti . |
| 4,115,492 | 9/1978 | Mahoney et al. . |
| 4,203,847 | 5/1980 | Grandine, 2nd . |
| 4,207,182 | 6/1980 | Marze . |
| 4,208,508 | 6/1980 | Hashino et al. . |
| 4,229,291 | 10/1980 | Walch et al. . |
| 4,230,583 | 10/1980 | Chiolle et al. . |
| 4,286,015 | 8/1981 | Yoshida et al. . |
| 4,311,587 | 1/1982 | Nose et al. . |
| 4,342,711 | 8/1982 | Joh et al. . |
| 4,351,860 | 9/1982 | Yoshida et al. . |
| 4,378,324 | 3/1983 | Makino et al. . |
| 4,432,875 | 2/1984 | Wrasidlo et al. . |
| 4,444,663 | 4/1984 | Aoyagi et al. . |
| 4,532,041 | 7/1985 | Shuey et al. . |
| 4,545,910 | 10/1985 | Marze . |
| 4,655,840 | 4/1987 | Wittwer et al. . |
| 4,664,859 | 5/1987 | Knoop . |
| 4,714,481 | 12/1987 | Matsura et al. . |
| 4,720,342 | 1/1988 | Takemura et al. . |
| 4,720,343 | 1/1988 | Walch et al. . |
| 4,722,795 | 2/1988 | Gohl et al. . |
| 4,746,474 | 5/1988 | Kohn . |
| 4,772,391 | 9/1988 | Baker . |
| 4,798,847 | 1/1989 | Roesink et al. . |
| 4,826,599 | 5/1989 | Bikson et al. . |
| 4,834,888 | 5/1989 | Polachegg . |
| 4,853,127 | 8/1989 | Le et al. . |
| 4,882,223 | 11/1989 | Aptel et al. . |
| 4,895,657 | 1/1990 | Polaschegg . |
| 4,900,449 | 2/1990 | Kraus et al. . |
| 4,900,502 | 2/1990 | Babcock et al. . |
| 4,906,375 | 3/1990 | Heilmann . |
| 4,923,598 | 5/1990 | Schal . |
| 4,933,083 | 6/1990 | Jones, Jr. . |
| 4,963,303 | 10/1990 | Anderson . |
| 4,964,990 | 10/1990 | Kraus et al. . |
| 4,983,191 | 1/1991 | Ekiner et al. . |
| 5,009,824 | 4/1991 | Walch et al. . |
| 5,015,270 | 5/1991 | Ekiner et al. . |
| 5,035,802 | 7/1991 | Yamasaki et al. . |
| 5,049,276 | 9/1991 | Sasaki . |
| 5,067,970 | 11/1991 | Wang et al. . |
| 5,076,925 | 12/1991 | Roesink et al. . |
| 5,085,676 | 2/1992 | Ekiner et al. . |
| 5,141,493 | 8/1992 | Jacobsen et al. . |
| 5,151,227 | 9/1992 | Nguyen et al. . |
| 5,160,672 | 11/1992 | Sasaki et al. . |
| 5,163,977 | 11/1992 | Jensvold et al. . |
| 5,181,940 | 1/1993 | Bikson et al. . |
| 5,247,434 | 9/1993 | Peterson et al. . |
| 5,266,197 | 11/1993 | Takata et al. . |
| 5,344,568 | 9/1994 | Kitaevich et al. . |
| 5,368,555 | 11/1994 | Sussman et al. . |
| 5,429,748 | 7/1995 | White et al. . |
| 5,443,728 | 8/1995 | Macheras et al. . |
| 5,480,554 | 1/1996 | Degen et al. . |

OTHER PUBLICATIONS

J. Bommer, et al., "No evidence for endotoxin transfer across high flux polysulfone membranes", Clin. Neph., vol. 27, No. 6, 1987, pp. 278–282).

S. Gordon et al., "Pyrogenic Reactions Associated with the Reuse of Disposable Hollow–Fiber Hemodialyzers", JAMA, Oct. 14, 1988, vol. 260, No. 14.

G. B. Harding et al., "Endotoxin and Bacterial Contamination of Dialysis Center Water and Dialysate: a Cross Sectional Survey", Intl. J. Artificial Organs, vol. 13, No. 1, 1990, pp. 39–43..

S. Gordon et al., "Pyrogenic Reactions in Patients Receiving Conventional, High–Efficiency, or High–Flux Hemodialysis Treatments with Bicarbonate Dialysate Containing High Concentrations of Bacteria and Endotoxin", JASN, Mar. 1992, vol. 2, No. 9, pp. 1436–1444.

S. Frinak et al., "Filtration of Dialysate Using an On–Line Dialysate Filter", Intl. J. Artificial Organs, vol. 14, No. 11, Nov. 1991, pp. 691–697.

C. Mion et al., "Sterile and Pyrogen–Free Bicarbonate Dialysate: A Necessity for Hemodialysis Today", Adv. Nephrol., 19:275–314, 1990.

L. Henderson, "Should Hemodialysis Fluid Be Sterile?", Seminars in Dialysis, vol. 6, No. 1, (Jan.–Feb.) 1993, pp. 26–27.

E. T. Rietschel and H. Brade, "Bacterial Endotoxins", Scientific American, Aug. 1992, 54–61.

J. Murray, "The Merits of LAL Testing", Contemporary Dialysis & Nephrology, Oct. 1991, pp. 20–22.

J. Baker, "Endotoxin Monitoring", Cont. Dialysis & Nephrology, Sep. 1991, pp. 44–45.

G. Cappelli, "Dialysate Contribution to Bio–Incompatibility in Hemodialysis, Cont. Dialysis & Nephrology", Dec. 1991, pp. 20–22.

K. Kumano, et al., "Methods of Minimizing Endotoxin Level in Dialysate", Dialysis & Translation, vol. 22, No. 3, Mar. 1993, pp. 147–152.

R. Vanholder, et al., "Endotoxin Transfer Through Dialysis Membranes: Small– Versus Large–Pore Membranes", Nephrol. Dial. Transplant (1992), 7: 333–339.

M. Laude–Sharp et al., "Induction of IL–1 During Hemodialysis: Transmembrane Passage of Intact Endotoxins (LPS)", Kidney Intl., vol. 38 (1990), pp. 1089–1094.

English Abstract for EP–488018. (Corresponding non–English document cited above.).

English Abstract for JP Sho 59–230604 (Counterpart to U.S. Pat. 4,532,041). (Corresponding non–English document cited above.).

English Abstract for JP Hei 3–178324 (Counterpart to U.S. Pat. 5,015,270). (Corresponding non–English document cited above.).

English Abstract for JP Hei 3–270721. (Corresponding non–English document cited above.).

English Abstract for JP Hei 4–227831 (Counterpart to U.S. Pat. 5,067,970). (Corresponding non–English document cited above.).

English Abstract for JP Hei 4–267934. (Corresponding non–English document cited above.).

CONNECTION WITH "OUTLET PORT ADAPTOR"

DIALYSATE FILTER INCLUDING AN ASYMMETRIC MICROPOROUS, HOLLOW FIBER MEMBRANE INCORPORATING A POLYIMIDE

Matter enclosed in heavy brackets [ ] appears in the original patent but forms no part of this reissue specification; matter printed in italics indicates the additions made by reissue.

This application is *a reissue application of Pat. No. 5,605,627 which is* a continuation-in-part of application Ser. No. 08/058,904 filed [Jun. 30, 1993, pending.] *May 6, 1993, U.S. Pat. No. 5,762,798,* which is a continuation-in-part of application Ser. No. 07/958,027 filed Oct. 7, 1992, now abandoned. Both prior applications are incorporated by reference herein, in their entirety.

BACKGROUND OF THE INVENTION

1. Field of the Invention

This invention relates generally to a dialysate filter which is easy to install, durable and cost effective. In particular, the invention relates to a dialysate filter which removes bacteria and endotoxins from a dialysate stream before it enters an artificial kidney. Still further, the dialysate filter of the present invention includes improved asymmetrical, microporous, hollow fibers incorporating a polyimide.

2. Description of the Related Art

A dialysate filter is a device which can be used in-line, between a dialysis apparatus and an artificial kidney (dialyzer) during hemodialysis treatments, to remove bacteria and endotoxins from the dialysate stream. Endotoxins are potentially lethal lipopolysaccharide (LPS) molecules which are released when gram-negative bacteria disintegrate or are destroyed.

Endotoxins can cause Pyrogenic Reactions (PRs) in dialysis patients either directly by passing through an artificial kidney membrane into the patient's bloodstream, or indirectly, by inducing a reaction across the artificial kidney membrane. PR(s) are one or more symptoms caused by exposure to endotoxins during dialysis, including fever, chills, hypotension, headache, myalgia, nausea and vomiting. Symptoms usually begin within 30–60 minutes after dialysis has begun, and, vanish shortly after dialysis is stopped. Indirect PR(s) may occur when endotoxins, while remaining trapped within the membrane, still influence changes in a dialysis patient's bloodstream without actually physically contacting the blood.

The role of endotoxins in the long-term morbidity and mortality of dialysis patients is unclear; however, we do know that endotoxins have the ability to stimulate monocytes to produce chemicals called cytokines. These cytokines induce fever and catabolism in dialysis patients. The present invention is a means for preventing PR's by using sterile, non-pyrogenic dialysate during dialysis treatment.

The prior art has promoted a number of alternatives for removing endotoxins from dialysate. These alternatives include an artificial kidney, ultrafiltration apparatuses, hemo-filters and in-line water filters. These alternatives suffer from a number of disadvantages including difficulty in use, expense and safety risks.

One significant safety risk of these modified devices is in the event of a fiber rupture, the filter can release enormous quantities of accumulated endotoxins into the dialysate stream. This may present too large a challenge for the dialyzer to overcome and the dialysis patient may suffer unpleasant consequences as a result. Also, if a portion of this assumed-to-be sterile dialysate solution is diverted and re-infused into the extracorporeal blood circuit, as may be done in hemodiafiltration, then bacteria and endotoxins may be injected directly into the patient's bloodstream.

Previous studies have made claims to endotoxin free dialysate. These claims may be not be completely accurate. Certain smaller endotoxin fragments may be Limulus Amebocyte Lysate assay (LAL) non-reactive. This means that much of the research done which has used LAL to measure passage of endotoxins through dialyzer membranes may be inaccurate. In other words, studies which claimed that no endotoxin passes through dialyzer membranes and used LAL to validate that claim may be inaccurate.

Also, there is some indication that certain smaller endotoxin fragments may pass through conventional dialyzer membranes when they may not pass through high flux membranes. This may be due to differing membrane properties such as mechanisms of adsorption, tortuous pathways, and ionic repulsion. In view of this endotoxins are not merely a concern for high flux dialysis, but for conventional and high efficiency dialysis also.

SUMMARY OF THE INVENTION

It is an object of the present invention to provide a dialysate filter which solves the problems outlined above that inhibited regular use of a dialysate filter, including difficult to use, expense and safety risks. The dialysate filter of the present invention enables the practitioner to quickly and easily install a dialysate filter outside the housing of a dialysis apparatus and thereby effectively monitor the filter and prevent dialysis machine complications. Dialysis machine complications include restricted dialysate flow, increased temperature and leaks. The dialysate filter of the present invention works well with a variety of dialysis machines and tolerates a wide variety of disinfecting chemicals without loss of integrity.

The filter of the present invention includes a housing having an inlet dialysate port, an outlet dialysate port and an access port which function to allow air to be removed and a disinfecting agent to be introduced. The housing contains an asymmetric microporous hollow fiber membrane which incorporates a polyimide.

The filter of the present invention is [preferrably] *preferably* a dialysate filter which is attached to a dialysis apparatus. The dialysis apparatus includes a housing, a dialyzer within the housing and a dialysate inlet port to the dialyzer. The apparatus is connected with the dialysate filter through a female to female connector. The filter is located upstream of the dialyzer outside the housing.

The dialysate filter of the present invention creates dialysate which is bacteria free and non-pyrogenic. The filter should be used as a preventative measure or in the event of Pyrogenic Reaction, a bacterial culture growth exceeding AAMI limits or a LAL assay indicating that endotoxin levels are in excess of 5 EU/ml or 1 ng/ml.

These and other objects and advantages of the present invention will become apparent during the course of the following detailed description and appended claims. The invention may best be understood with reference to the accompanying drawings, disclosure and examples wherein an illustrative embodiment is shown.

DETAILED DESCRIPTION

The present invention is directed to a filter membrane, a dialysate filter and a dialysis apparatus. Although the membrane and dialysate filter are discussed in connection with their use in dialysis, the skilled artisan would clearly recognize the applicability of the membrane and filter to other technology areas. These areas include water filtration, as a polishing filter for pharmaceutical production, as a plasma filtering device, as a chemofilter, as a hemoconcentrator, and the like.

Dialysate as used herein refers to the final solution, blended within the dialysis apparatus, from sodium bicarbonate concentrate, acid electrolyte concentrate, and ultrapure water, which flows in a single pass through the dialysate filter and artificial kidney and then finally to drain.

An in-line filter, installed in the dialysate line of a dialysis apparatus, will block passage of most endotoxins contained within reverse osmosis water or the final dialysate stream of the dialysis apparatus. The filter will prevent high loads of endotoxin from reaching the dialysate compartment of the artificial kidney during dialysis and causing Pyrogen Reactions in dialysis patients.

The filter membrane of the present invention produces a dialysate which is bacteria free and non-pyrogenic. "Bacteria free" as used herein means that no bacteria is detectable as determined by a filter effluent sample's lack of bacterial growth in an optimum environment for growth. "Non-pyrogenic" means that no endotoxins are detectable as determined by the gel-clot method of Limulus Amebocyte Lysate (LAL) assay of filtrate, or levels of pyrogenic material are so low no PR will occur during dialysis. "Filtrate" refers to the dialysate outflow or effluent from the filter.

The filter membrane of the present invention is particularly well suited for these applications as it is easy to install, maintain and sterilize. The filter membrane in one embodiment of the present invention will tolerate a dialysate flow of from 300 ml/min to 1000 ml/min, and will also tolerate a wide variety of disinfection regimens and chemicals.

Figure 2:
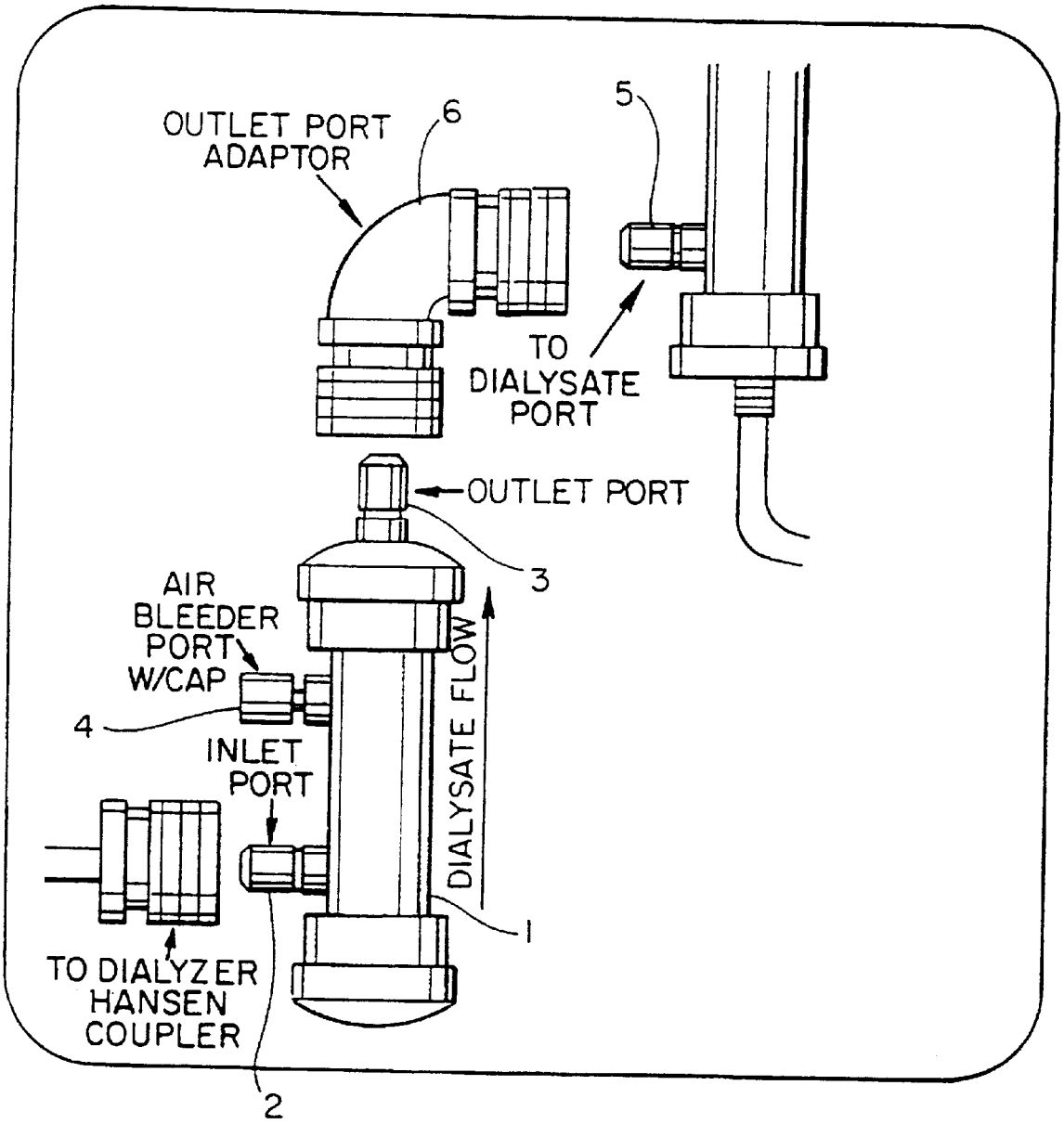
FIG. 2 depicts a dialysate filter of the present invention and its connectors.

As seen in FIG. 2, the dialysate filter of the present invention is comprised of a housing (1) having a dialysate inlet port (2), a dialysate outlet port (3) and an access port (4). Inside the housing is a filter comprising a bundle of fibrous-membranes.

The housing can be made of any appropriate material which includes polycarbonate, polypropylene, polyethylene, mixtures thereof and the like. Preferably polycarbonate forms the housing.

The housing is connected to the dialysate inlet port on a dialysis apparatus (5) through a female to female "Hansen" or "Walther" connector (6). The connector (6) may be attached directly to the dialysate outlet port of the filter (3) or may be connected via a hose or other interposed connection means to the outlet port (3). The connector (6) may take any shape but preferably is a straight-line connect, a 45° angle connect or a 90° angle connect. More preferably, the connector is a 90° angle connect.

The fiber membrane contained within the housing may be made of any highly permeable filter medium, for example, polymeric fibrous membranes. These membranes can be formed of polysulfone, polycarbonate, polyimide and the like. The filter is preferrably made up of asymmetric microporous hollow fiber membranes.

In one preferred embodiment of the present invention, the filter contains asymmetrical microporous, hollow fiber membranes that include a polyimide polymer that is highly polar. We define microporous to mean membranes having a pore size ranging from about 0.005–0.2$\mu$m. We also define "flux" or "water permeability" to mean a measure of the volume of water passed by the hollow fiber membrane under pressure for a given time and area. "Rewetting" and similar words such as rewettable, rewettability, etc., as used herein, is a description of the ability of a membrane to maintain a particular level of flux or water permeability after either cycles of wetting and drying the membrane or after steam or chemical sterilization. "Asymmetric" means that the pore size of the fiber varies from smaller to larger from the inner barrier layer to the outer sponge-like layer, respectively. "Uniformly porous" and "sponge-like" means that the porosity of the hollow fiber membrane is homogeneous throughout. In addition, "solvents with respect to the polymer" are typically aprotic solvents while "non-solvents with respect to the polymer" are typically protic solvents. "Anti-solvent" is a nonsolvent with respect to the polymer and is used herein when referring to additional nonsolvents that are added to the polymeric solution. "Nonsolvents," on the other hand, are also nonsolvents with respect to the polymer, but is used herein when referring to nonsolvents added to the precipitating solution.

The highly polar polymer in accordance with the present invention is preferably an aromatic polyimide that when precipitated as a membrane is immediately wettable without the use of polymer additives or surfactants. The preferred polyimide in accordance with the present invention is disclosed in U.S. Pat. No. 3,708,458 to Alberino which is incorporated herein by reference, in its entirety. The polyimide is prepared from benzophenone3,3',4,4'tetracarboxylic acid dianhydride and a mixture of 4,4'-methylenebis(phenylisocyanate) and toluene diisocyanate (2,4- or 2,6-isomer) or mixtures thereof. The polyimide includes the recurring group:

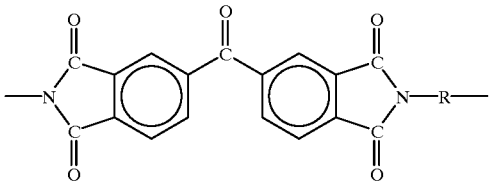

wherein 10% to 90% of the R groups are

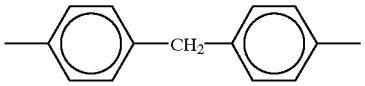

and the remaining R groups include either

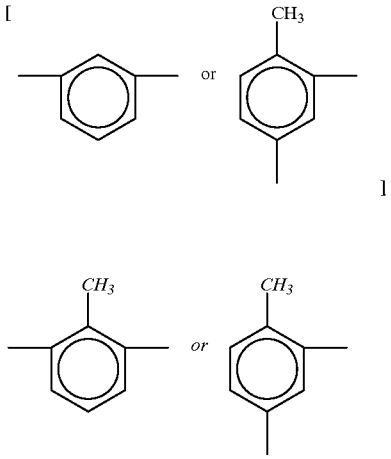

The aromatic iso- and diisocyanates may be substituted by their amine analogs. The CAS Registry No. of the preferred polyimide is 58698-66-1. The polyimide is available from Lenzing Corp. (Austria) under the P84 and/or HP P84 (high purity) marks. In an alternative embodiment, a polymer based on the phenylindane diamine; 5(6)-amino-1-(4'-aminophenyl)-1,3-trimethylindane with a CAS Registry No. of 62929-02-6 may be used. The alternative embodiment polymer is available from Ciba-Geigy Corporation (Hawthorne, N.Y.) under the Matrimid 5218 mark.

The structure of the polymer repeating unit is believed to consist of:

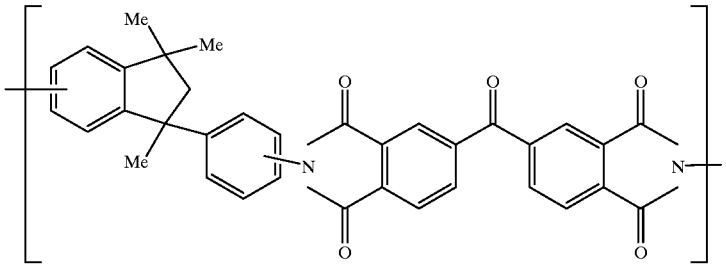

The alternative preferred embodiment may be prepared by the methods disclosed in U.S. Pat. No. 3,856,752.

The polyimide polymers useful in accordance with the present invention preferably have a molecular weight of about 30,000 to 125,000 daltons. More preferably, the molecular weight is about 35,000 to 115,000 daltons and most preferably, the molecular weight is about 40,000 to 105,000 daltons.

As stated previously, no additional additives, such as polyvinylpyrrolidone, polyethylene glycol, glycerine, cellulose or starch derivatives or amphoteric, zwitterionic, nonionic, anionic, or cationic surfactants, are needed to produce a hollow fiber membrane that wets immediately upon contact with dialysate, blood, water and other aqueous solutions and maintains the rewettability for at least 6–7 sterilizations by steam or chemicals. Because no additional polymers are needed to make the resultant fiber wettable, the choice of solvents, including nonsolvent combinations at specific ratios, for use as the precipitating solution is critical in influencing the hydrophilicity, structure and porosity of the fiber. In addition, the elimination of additives in the polymeric dope solution decreases and virtually eliminates all but trace amounts of solids and/or oxidizable material that is leachable from the resultant fiber. Further, the structural integrity of the resultant hollow fiber membrane is more stable after the removal of the solvent and/or antisolvents and nonsolvents.

Initially, the polyimide polymer is dissolved in a solvent including solvent/antisolvent combinations. Preferably, this solvent is also miscible with water. A representative, non-limiting list of solvents useful in the invention includes dimethylformamide (DMF), dimethylsulfoxide (DMSO), dimethylacetamide (DMA), n-methylpyrrolidone, and mixtures thereof. Preferably, the solvent is DMF, an aprotic solvent. Depending on the desired properties of the hollow fiber, a small amount of an antisolvent may be added in small quantities to the primary solvent that is used. The addition of an antisolvent in the polymer forming solution will enhance the desired precipitate characteristics of the polymer during fiber formation. For example, adding acetic acid in the amount of 4–7 wt. % ensures that the fiber has a uniform sponge-like structure, free of voids, large vacuous spaces extending from the inner membrane wall to the outer membrane wall that can permit the passage of large molecular weight molecules if the void pierces the inner and/or outer membrane wall. Alternatively, additional amounts of solids may be added to the polymer solution up to 25.0 wt. % to solve this problem. The homogeneous, sponge-like structure may also be achieved in accordance with the process and formulations described herein.

Figure 3A:
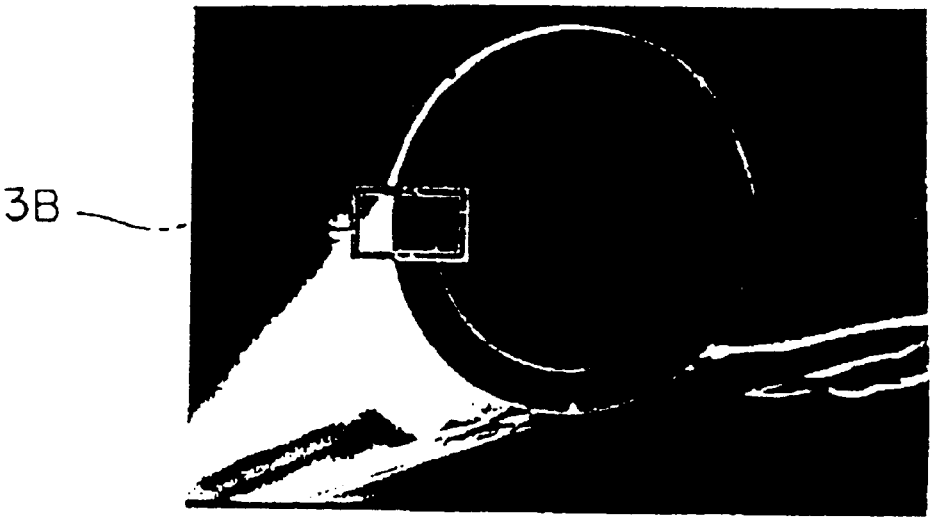
FIG. 3A is an enlarged, microscopic, cross-sectional view of the hollow fiber membrane in accordance with the present invention illustrating the "homogeneous sponge-like" structure.
Figure 3B:
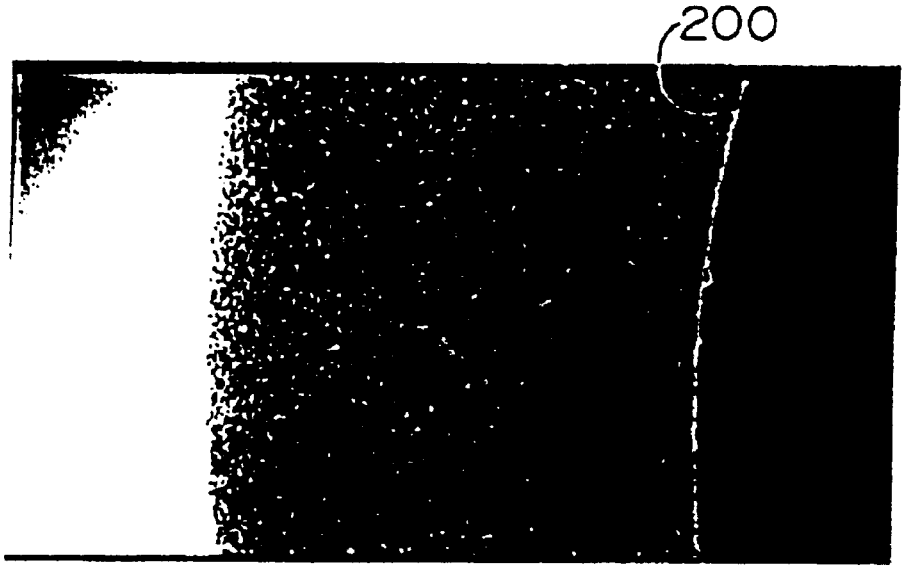
FIG. 3B is a greatly enlarged view thereof taken from the area enclosed by box 3B in FIG. 3A.
Figure 4:
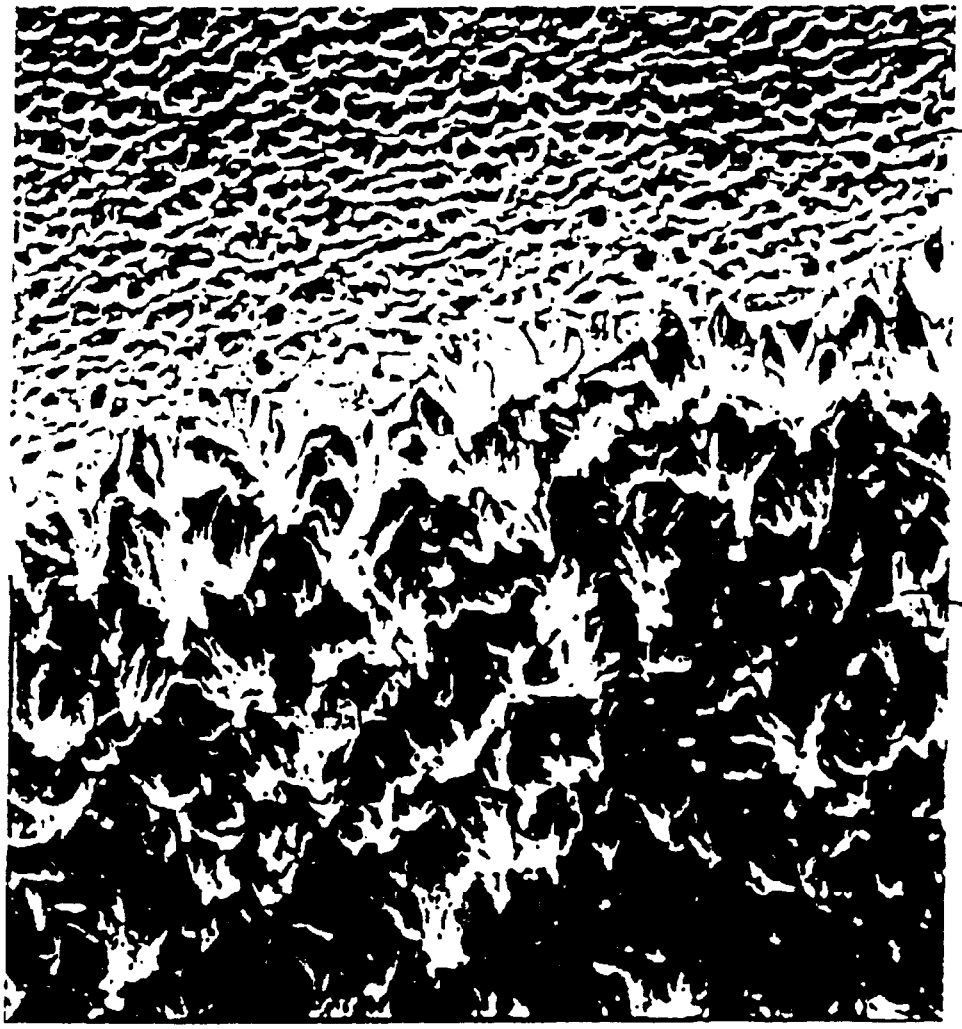
FIG. 4 is an enlarged detailed view of the hollow fiber membrane in accordance with the present invention illustrating the homogeneous sponge-like structure taken at a 45° angle of cross-section.
Figure 5A:
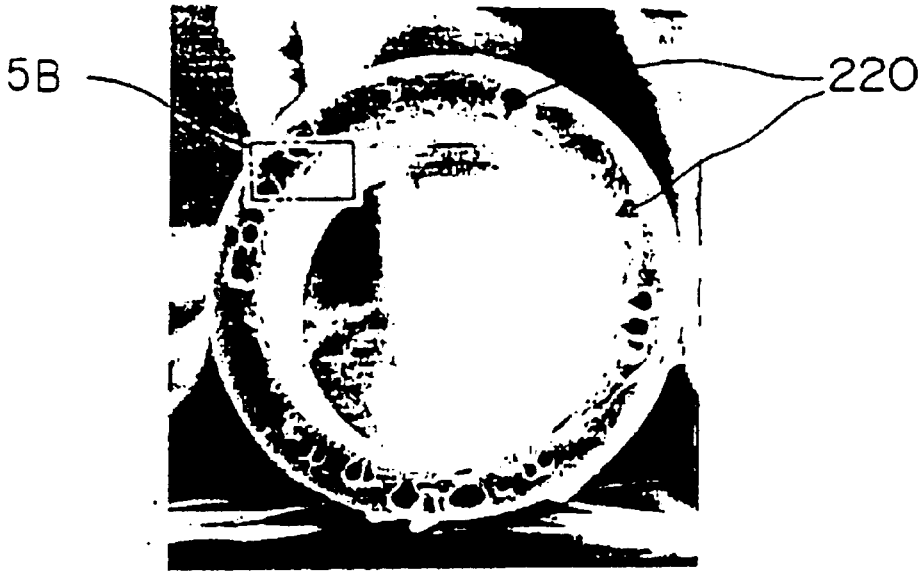
FIG. 5A is an enlarged, microscopic cross-sectional view of prior art hollow fiber membranes illustrating "voids."
Figure 5B:
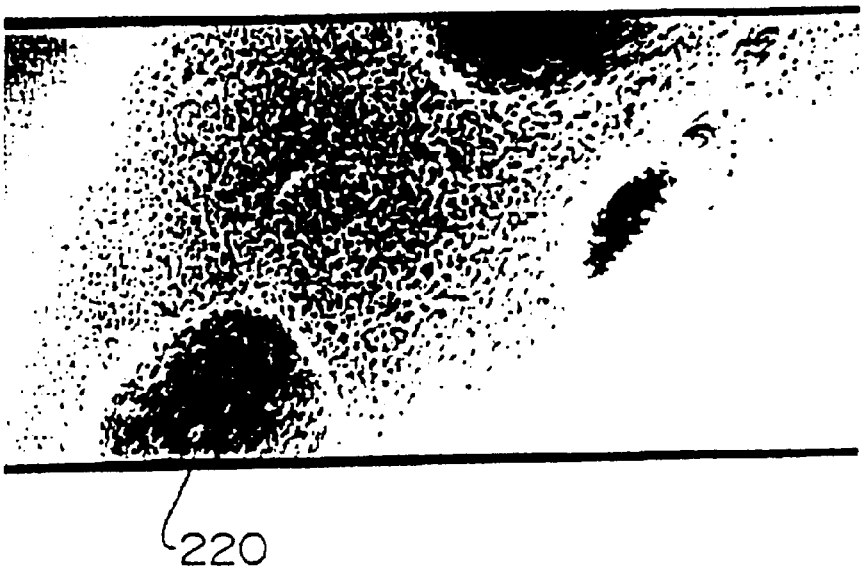
FIG. 5B is a greatly enlarged detail view thereof taken from the area enclosed by box 5B in FIG. 5A.

FIG. 3 depicts a cross section of a hollow fiber membrane in accordance with the present invention magnified 130× taken on a Hitachi 5-800 scanning electron microscope. FIG. 3B which is a 10× magnification (1300×) of the area enclosed by box 4B in FIG. 3A and illustrates the "uniform sponge-like structure 200 of hollow fiber membranes in accordance with the present invention. FIG. 4 is a 10,000× view taken at a 45° angle of cross-section of hollow fibers in accordance with the present invention showing the outer membrane wall 210 and the sponge-like inner composition 215. "Voids" 220, which characterize many hollow fiber membranes, may be seen by referring to FIGS. 5A (130×) and 5B (1300×). The absence of voids in the formed hollow fiber membrane results in a mechanically stronger fiber with enhanced diffusion rates.

Preferably, about 15–25 wt-%, more preferably, about 16–20 wt-%, and most preferably, about 17–19 wt-% of the fiber forming polyimide polymer is dissolved in the dimethylformamide solvent. When less than 15 wt-% of the polyimide polymer is used, the fibers formed may not be strong enough to withstand the stresses involved in the high speed process in the preferred method of manufacturing the fiber membrane used in the present invention. Further, the fibers lack integrity due to the weakness from the voids in the fiber walls.

Higher polyimide solids may be employed in organic solvent systems if spinerette housings, feed lines, polymer solution tanks are heated. Upon heating, the viscosity of the polymer solution is lowered, allowing otherwise unusable polymer solution formulations to be spun. Depending upon the composition of the precipitating solution the skilled practitioner chooses, heating and/or cooking the system may influence the morphology and performance characteristics of the resultant fiber membrane.

The polymeric solution has a viscosity of about 1500–5000 cps, preferably about 2000–4000 cps, and most preferably about 3600 to 4900 cps at 25° C., as measured on a Brookfield (LV) viscometer. The solution is preferably filtered to remove any entrained particles (contaminants or undissolved components) to prevent apparatus blockage.

The polymeric solution is spun from the outer, annular orifice of a tube-in-orifice spinerette. A precipitating solution is delivered to the tube of the spinerette. The precipitating solution includes a solvent with respect to the polymer and a non-solvent with respect to the polymer or a variety of non-solvents. The composition of the precipitating solution is critical because it affects the porosity, degree of uniform sponge-like structure, clearance, tensile strength, wall thickness, inner and outer diameters and flux properties of the fiber.

Figure 6:
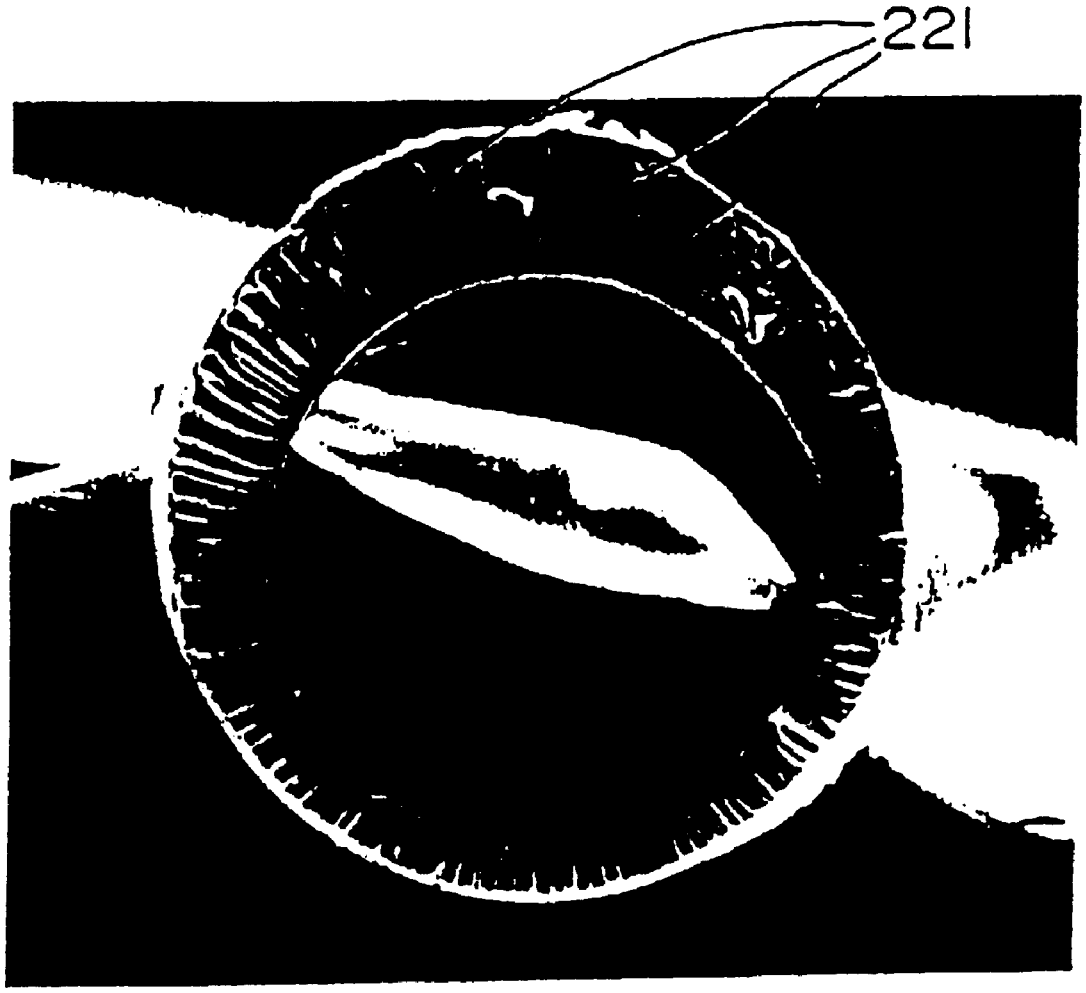
FIG. 6 is an enlarged, microscopic cross-sectional view of hollow fiber membranes with voids.

For example, as the weight percent of the solvent with respect to the polymer increases, fiber formation is impaired and is characterized by a "glassy" weaker structure and it becomes increasingly difficult to "pull" the fiber. Conversely, as the weight percent of the solvent with respect to the polymer decreases and the weight percent of water and/or other non-solvents with respect to the polymer increases, voids are seen in the fiber structure which may allow high molecular weight molecules to pass through the fiber if they pierce the outer membrane wall. This may best be seen in FIG. 6 which illustrates a fiber cross-section magnified 130× with voids 221 that resulted from using a precipitating solution with an increased weight percent of non-solvent with respect to the polymer. In addition, as the weight percent of water and/or other non-solvents with respect to the polymer increases, a low pore density on the outer fiber wall and a tighter closed inner wall with a low flux is seen. It will therefore be appreciated by those skilled in the art that the selection of the composition of the precipitating solution is crucial.

The composition of the precipitating solution effective to produce a hollow fiber membrane for use in hemodialysis, as well as, water filters, autologous blood filters, and plasma filters is illustrated below in Table I.

TABLE I

| | Preferred | More Preferred | Most Preferred |
|---|---|---|---|
| Solvent with respect to polymer | 50–99 wt. % | 60–95 wt. % | 75–90 wt. % |
| Water | 35–1 wt. % | 30–5 wt. % | 20–10 wt. % |
| Add'l Non-Solvents with respect to polymer | 15–0 wt. % | 10–0 wt. % | 5–0 wt. % |

The table above is merely offered to guide the practitioner in formulating precipitating solution. Indeed, the practitioner may decide that it is advantageous to operate in a "Preferred" range for one component while operating in a "Most Preferred" range for another. In addition, depending on which formulation of precipitating solution the practitioner selects, he or she may also vary the percent solids in the polymer solution to obtain a fiber of the desired characteristics.

The water which may be used in the precipitating solution may be tap water, deionized water or water which is a product of reverse osmosis. Preferably the water has first been treated by reverse osmosis.

As stated previously, the solvent (with respect to the polymer) used in the precipitating solution is dimethylformamide (DMF), dimethylsulfoxide (DMSO) dimethylacetamide (DMA), n-methylpyrrolidone and mixtures thereof. Preferably, the solvent is the same as that used in the polymeric fiber forming solution. More preferably, the solvent is DMA or DMF. Most preferably, the solvent is DMF.

Additional combinations of solvents and non-solvents, which may or may not contain salts, may be used so long as they are miscible with dimethylformamide, dimethylsulfoxide, dimethylacetamide, n-methylpyrrolidone and mixtures thereof. A representative, non-limiting list of non-solvents (with respect to the polymer) that may be used in the precipitating solution are acetic acid, isopropanol, water, glycerol, acetic anhydride, and ethanol.

The proportions of the water, and other non-solvents (e.g. alcohol) which may make up the precipitating solution influence the morphology, clearance, permeability, and selectivity characteristics of the hollow fiber membrane. In particular, the total absence of a solvent with respect to the polymer in the precipitating solution may result in a small number of pores in the fiber wall as well as lower flux. Further, water is clearly an important ingredient in the precipitating solution used in this membrane formation process.

Because the addition of water affects the performance characteristics of the resultant fiber membrane it is generally preferred that the proportion of water in the precipitating solution be about 1–35 wt. %, to ensure proper fiber performance characteristics. Less than about 10 wt. % of water may result in the polymeric solution precipitating too slowly forming a fiber with increased pore size. This is desirable to form a fiber for use in water filters but would not, for example, form a fiber suitable for use as a dialyzer fiber. Conversely, a concentration of water greater than about 35 wt. % results in a fiber with lower pore density on the outside and a tighter closed inner wall with a general decrease in flux. However, when the proportion of water falls within 1–35 wt. %, we see enhanced uniformity in the desirable sponge-like structure and the hollow fiber membrane is characterized by the complete absence of voids. This uniformity results in more overall uniform flux with respect to all types of filters and tighter controls with respect to molecular weight cutoffs in dialyzer applications.

The hollow fiber membranes may be formed using tube-in-orifice spinning procedures as disclosed in the [copending] *abandoned*, commonly assigned applications Ser. No. 07/684,585, filed Apr. 1, 1991 entitled "Improved Fiber Spinning Process for the Preparation of Asymmetrical Microporous Hollow Fibers" and Ser. No. 07/902,389, filed Jun. 23, 1992 entitled "Hollow Fiber Membrane Incorporating a Surfactant and Process for Preparing Same," the disclosures of which are hereby incorporated by reference.

Initially, the highly polar polymer is diluted in DMF. Depending on the desired properties and characteristics of the hollow fiber, a small amount of a non-solvent (with respect to the polymer) (also called anti-solvents) other than water may be added instead of using pure DMF solvent. This may enhance the precipitation of the polymer in the fiber formation. For example, the addition of 4–7 wt. % glacial acetic acid to the polymer/DMF solution enhances the uniform sponge-like structure of the resultant fiber and the fiber is further characterized by the complete absence of voids.

The polymeric dope solution is pumped, filtered and directed to the outer, ring orifice of a tube-in-orifice spinerette. At the same time, the precipitating solution is pumped to the inner coaxial tube of the spinerette. These two solutions are then delivered from the spinerette in a manner such that the polymer dope forms an annular sheath surrounding a flow of precipitating solution within the annulus. Preferably, the spinerette head is maintained at a temperature of about 5°–85° C., more preferably, about 15°–25° C., and most preferably, 23°–24° C. The 23.9° C. polymeric dope is subjected to a pressure of about 0–1400 kPa, more preferably, about 140–1000 kPa, and most preferably, about 150–750 kPa. In a preferred embodiment, the polymer dope is spun through a ring orifice having an outside diameter of about 0.018 to 0.040 inches (about 460 to 1,016 microns) and an inside diameter of about 0.008 to 0.010 inches (about 200 to 280 microns).

At the same time, precipitating solution is pumped through the tube of the spinerette at a pressure of about 0–1000 kPa, preferably about 0–100 kPa, and most preferably, about 1–20 kPa. In a preferred embodiment, the precipitating solution or diluent solution is delivered through a tube having an outside diameter of substantially about 0.010 inches (about 254 microns) and an inside diameter of substantially about 0.004 to 0.005 inches (about 100 to 127 microns).

In a preferred embodiment, in order to produce a hollow fiber having an approximately 190–230 micron inside diameter and a wall size of 30–45 microns, the polymer dope is delivered to the spinerette at a rate of substantially about 1.0–10 mL/min, more preferably, about 2–5 mL/min, most preferably, about 3–4.5 mL/min, and the precipitating solution is delivered at a rate of at least about 1.0–10 mL/min, more preferably, about 2–5 mL/min, and most preferably, about 2–3 mL/min. The spinerette is oriented in a manner such that fiber production is driven by fluid flow and by removal from the spinerette by gravity effects. Preferably, the fiber emerges from the spinerette and is pulled by gravity and the take-up speed in a nearly vertical direction downwards.

In order to provide satisfactory fibers in the practice of the invention, laminar fluid flow should be maintained both within the spinerette head for the polymeric solution and the precipitating solution which interact to precipitate the formed fiber. If turbulent flow is present in the spinerette head, especially within the channels which convey the polymeric dope, gas pockets may develop and ultimately form large voids in the spun fiber. Turbulent flow-within the spun fluids may also result in voids within the fiber.

It is helpful to visualize the spinerette dimensions by resort to ratios of the annular orifice for passage of the polymeric dope and the coaxial tubular orifice for passage of the diluent or precipitating solution. One helpful ratio is the ratio of the cross-sectional area of the annular orifice to tubular orifice. Preferably, the ratio is greater than about 1:1, more preferably, the ratio is about 3:1 to 25:1, and most preferably, the ratio of the annular orifice to tubular orifice cross-sectional area is about 4:1 to 15:1.

Another helpful dimensional ratio is the annular ring thickness to tube inside diameter. Preferably, the ratio is greater than about 1:1, more preferably, the ratio is about 1.5:1 to 7:1, and most preferably, the ratio of the annular ring thickness to tube inside diameter is about 2:1 to 6:1.

A third helpful dimensional ratio is the outside diameter of the annular orifice to tube inside diameter. Preferably, this ratio is greater than about 2:1, more preferably, the ratio is about 3:1 to 10:1, and most preferably, the ratio of the annular outside diameter to tube inside diameter is about 4:1 to 8:1.

As the fiber emerges from the spinerette, it drops in a substantially downward vertical direction over a distance of about 0.1–10 m, more preferably, about 0.5 to 2.0 m, and most preferably, about 0.5 to 1.5 m. This allows the precipitating solution to substantially precipitate the polymer in the annular dope solution forming the solid fiber capillary before it is immersed in a quenching solution. Between the spinerette and the quenching bath, the fiber drops through the atmosphere, air, air with a particular relative humidity, an augmented atmosphere, e.g., a mixture of air or air with a particular relative humidity and a gas, an inert gas, or a mixture thereof. Preferably, for ease in processing and to produce a high quality fiber, the fiber drops through air maintained at a temperature of 0° C. to 100° C., more preferably, the air is maintained at a temperature of 5° C. to 50° C. and most preferably at 15° C. to 25° C. Preferably the air is also maintained at a relative humidity of substantially about 10% to 99%, more preferably from substantially about 20% to 80% and most preferably from substantially about 40% to 65%. This gaseous atmosphere may be relatively stagnant, or there can be fluid flow. Preferably, the flow rate is sufficient to allow complete air change over in the spinning environment once every 30 minutes. In one preferred embodiment, the gas flow is about 10 L/min. In an alternative embodiment, the fiber may be dropped directly into the quenching bath.

The fiber is submerged in a tank comprising water and 0–10 wt. % other materials. Again, the water may be tap, or any purified water including deionized water, or the product of a reverse osmosis process. The temperature of the quenching bath is preferably between about 0° C. to 100° C., more preferably, about 15° C. to 45° C., and most preferably, about 35° C. The water temperature directly affects-the performance of the fiber. Lower temperatures can reduce the flux of the resulting fiber. Increasing the quenching bath temperature can increase the flux of the fiber.

The fiber is preferably immersed in the quenching bath for a period of about 0.1 to 10 seconds, preferably about 0.1 to 5 seconds, and most preferably, about 1 second. This residence time permits the full precipitation of the polyimide polymer to form the microporous hollow fiber.

After the quenching bath, the fiber may be further rinsed to remove any remaining solvents. This rinsing may be accomplished in a water bath arrangement. Preferably, the additional rinse is achieved in a water bath having a water temperature of about 0° C.–100° C., more preferably, about 15° C.–45° C., and most preferably, about 35° C. The fiber is then wound on a take-up reel. The take-up reel is preferably rotating at a speed such that the fiber is being wound at about 90–175% of the rate at which it is being formed at the spinerette or, in other words, at approximately about 150–250 ft/min (about 45–77 m/min). More preferably, the fiber is being wound at a rate substantially equal to that at which it is being produced. In other words, the fiber is taken up with enough speed (i) to create a fiber of the desired size and (ii) to apply sufficient tension to the fiber such that it will remain taut in the take-up guide unaffected by ambient air currents, i.e. there is no "draft."

The hollow fibers may then be dried by any method appropriate to general manufacturing procedures including but not limited to air, heat, vacuum, or any combination thereof. The hollow fibers may be further processed to form useful articles including hemodialyzer cartridges, hemofilters, blood filters, water filters, etc., having improved performance levels.

In the present invention, polyimide fibers are preferred over polysulfone because they have a lower pressure drop across the filter, i.e., they are more permeable.

The filter of the present invention preferably contains a bundle of fibers which are anchored within the housing by a potting composition. The preferred potting composition of the present invention is urethane. The fiber bundle within the housing should contain sufficient fibers to achieve the objectives of the filter as disclosed, however, the skilled practitioner would understand that the number of fibers may be modified so that the necessary permeability of the filter is maintained. The number of fibers is preferably between 4500 and 5000 fibers per bundle.

As described above, the filter of the present invention is preferably attached via a Hansen connector. In one preferred embodiment, the filter is attached to the dialysis apparatus at the inlet dialysate port outside the housing immediately upstream of the artificial kidney or dialyzer.

The filter of the present invention may be installed within the dialysis apparatus housing, however, it will be more difficult to clean and evaluate based upon that location. The filter may also be placed further upstream of the dialyzer, however, upstream placement runs an added risk of recontamination of dialysis fluids.

By placing the filter outside the housing, the pressure drop across the filter can be easily monitored. The pressure drop is indicative of flow characteristics of the dialysate and can indicate dialysis machine complications, including restricted flow, leaks, or an increase in temperature. With the external placement of the filter in the preferred embodiment of the present invention, the filter may be installed or replaced while a dialysis treatment is ongoing. Accordingly, in the event of a rupture of the filter, the unit can be quickly and easily replaced without any added risk to the patient.

The filter can be used with any hemodialysis machine but is preferably used with single pass ultrafiltration controlled hemodialysis machines.

The preferred dialysate filter of the present invention has the properties set forth in the Table below:

TABLE II

| | |
|---|---|
| Fiber | Hydrophilic Polymer |
| Number of Fibers | 5000 |
| Effective Surface Area | 0.3 $m^2$ |
| Initial Pressure drop (Q = 500 ml/min) | 60 mmHg (in dialysate) |
| Maximum Pressure Drop | 160 mmHg (in dialysate) |
| Total Fluid Volume | 72 ml |
| Overall Unit Length | 192 mm |
| Unit Weight (Dry) | 145 g |
| Outer Case Material | Polycarbonate |
| Potting Compound | Polyurethane |
| O-Ring | Silicone |
| Dialysis Fluid Connectors | Hansen or Walther Connectors |

The filters should be stored between 0° and 35° C., and excessive changes in humidity should be avoided.

The filter of the present invention should be disinfected daily. Preferred disinfectants include acetic acid based sterilants available under the tradenames Actril and Renalin Cold Sterilant, bleach and heat treatment. The filter is replaced preferably within 30 days. The filter should also be replaced in the event the pressure across the filter rises or drops to unacceptable levels. Preferably, the filter is replaced if the pressure drop across the filter is greater than 155 mmHg (3 PSI) or less than 52 mmHg (1 PSI).

EXAMPLES

The following specific examples which contain the best mode, can be used to further illustrate the invention. These examples are merely illustrative of the invention and do not limit its scope.

Examples 1–7 characterize and describe how to prepare the polyimide fibers according to one preferred embodiment of the present invention. Examples 8–29 describe the preparation, testing, cleaning and use of the filters of the present invention.

Example 1

A polymeric dope solution was formed by dissolving 17.5 wt. % of P84 in dimethylformamide. The material was filtered and then pumped to a tube-in-orifice spinerette at a rate of 4.50 mL/min and at a temperature of 24° C. Simultaneously, a precipitating solution consisting of 80 wt. % dimethylformamide and 20 wt. % reverse osmosis deionized water was mixed, filtered and delivered to the spinerette at a temperature of 24° C. and a rate of 2.75 mL/min.

The polymeric dope solution was delivered through the outer, annular orifice of the spinerette, which orifice had an outside dimension of about 0.022 to 0.025 inches (about 560 $\mu$m) and an inside dimension of about 0.010 inches (about 254 $\mu$m). The precipitating solution was delivered through a tube-in-orifice within the annular orifice, which tube-in-orifice had an inside diameter of about 0.005 inches (about 127 $\mu$m). The spinerette head was maintained at 24° C. The spinerette discharged the polymeric solution and precipitating solution downward into ambient atmosphere for a distance of about 1.5 meters into a quenching bath maintained at 32° C. Formed fiber material was wound on a take-up reel at a rate of 70 m/min. The fiber was then removed from the take-up wheel, cut, bundled, soaked in a water bath at 32° C. for 10 hours, dried and tested.

Test Data #1

Fiber membranes prepared by the method recited in Example 1 had sieving coefficients of 0.0 for albumin, 1.0 for myoglobin and 1.0 for inulin.

| Blood Fl. | Urea | Creatinine | Phos-phorous | B-12 | Cytochrome C |
|---|---|---|---|---|---|
| 200 mL/m | 179.4 | 164.9 | 156.5 | 87.4 | 129.9 |
| 300 mL/m | 225.0 | 198.5 | 182.6 | 93.8 | 143.0 |
| 400 mL/m | 244.8 | 212.5 | 208.7 | 95.7 | 146.8 |

Example 2

The method for preparing fiber as in Example 1 was repeated using a precipitating solution of 81 wt. % DMF and 19 wt. % deionized water.

Test Data #2

Resultant fiber membranes had sieving coefficients of 0.0 for albumin, 1.0 for myoglobin, and 1.0 for inulin.

| Blood Fl. | Urea | Creatinine | Phos-phorous | B-12 | Cytochrome C |
|---|---|---|---|---|---|
| 200 mL/m | 188.1 | 178.3 | 166.7 | 88.5 | 156.9 |
| 300 mL/m | 249.6 | 223.4 | 212.5 | 95.4 | 178.7 |
| 400 mL/m | 281.5 | 246.7 | 233.5 | 116.0 | 184.0 |

Example 3

The method employed in Example 1 was repeated using 17.0 wt. % of the P84 polyimide polymer and 83 wt. % DMF. The precipitating solution comprised 81 wt. % DMF and 19.0 wt. % deionized water. Sieving-coefficients were similar to the Test Data obtained for Examples 1 and 2 above.

| Blood Fl. | Urea | Creatinine | Phos-phorous | B-12 | Cytochrome C |
|---|---|---|---|---|---|
| 200 mL/m | 190.7 | 178.4 | 166.7 | — | 162.9 |
| 300 mL/m | 255.2 | 232.45 | 228.0 | — | 185.7 |
| 400 mL/m | 287.3 | 256.9 | 240.0 | — | 188.8 |

Example 4

Fibers for use in a water filter were manufactured in the following manner. A polymeric dope solution was formed by dissolving 19.0 wt. % of Matrimid 5218 in 81.0 wt. % DMF. The material was filtered and then pumped to a tube-in-orifice spinerette at a rate of 2.9 mL/min at a temperature of 23° C. Simultaneously, a precipitating solution consisting of 85.5 wt. % DMF and 14.5 wt. % water was mixed, filtered and delivered to the spinerette at a temperature of 23° C. and a rate of 3.0 mL/min.

The polymeric dope solution was delivered through the outer, annular orifice of the spinerette having an outside diameter of 940 $\mu$m and an inside diameter of 254 $\mu$m. The precipitating solution was delivered through a tube-in-orifice within the annular orifice having an inside diameter of about 127 $\mu$m. The spinerette head was maintained at about 23° C. The spinerette discharged the column of polymeric/solution and precipitating solution downward for a distance of about 0.81 m into a quenching water bath maintained at a temperature of 35° C. The fiber was wound on a take-up reel at a rate of about 45 m/min. Cut bundles were soaked in a 46° C. water bath for 16 hours. Fiber bundles were dried and tested. Based on a 0.05 $m^2$ test mat, at 5 psi, water permeability was calculated to be 500 mL/(hr×$m^2$×mmHg).

Example 5

Fibers for use in a plasma filter were manufactured in the following manner. The method for preparing fiber as in Example 4 was repeated using a polymeric dope solution consisting of 16.75% P84 polymer and 83.25 wt. % DMF. The precipitating solution included 85.5 wt. % DMF and 14.5 wt. % deionized water. Fibers had a sieving coefficient of 0.65 using a 0.1% solution of fluorescein isothiocyanate dextran (Sigma), a molecular weight marker of approximately 500,000 Daltons. Water permeability was in excess of 900 (mL/hr/mmHg/$m^2$).

Example 6

Fibers for use in a water filter were manufactured in the following manner. A polymeric dope solution was formed by dissolving 16.75 wt. % P84 polymer in 83.25 wt. % DMF. The material was filtered and then pumped to a tube-in-orifice spinerette at a rate of 4.5 mL/min at a temperature of 23° C. Simultaneously, a precipitating solution consisting of 85.5 wt. % DMF and 14.5 wt. % water was mixed, filtered and delivered to the spinerette at a temperature of 23° C. and a rate of 3.0 mL/min.

Fibers were further processed in accordance with the method of Example 4. [Fibers were further processed in accordance with the method of Example 4.] A water filter (1.5 $m^2$ of fiber) containing the fibers manufactured using the above formulation was tested for water permeability. At 8.6 psi, filters had a water permeability of 1020 ml/(hr×$m^2$×mmHg). At 10.0 psi, filters had a water permeability of 1320 ml(hr×$m^2$×mmHg).

Example 7

Fibers for use in water filters were prepared in the following manner. A polymeric dope solution was formed by dissolving 15.2 wt. % P84 polyimide polymer in 79.80 wt. % DMF and 5.0 wt. % glacial acetic acid. The material was filtered and pumped to a tube-in-orifice spinerette at a rate of 4.1 mL/min. A precipitating solution comprised of 50 wt. % DMF and 50 wt. % glacial acetic acid was mixed, filtered and delivered to the spinerette at a rate of 4.5 mL/min.

The polymeric dope solution was delivered through the outer, annular orifice of the spinerette having an outside dimension of about 0.029 inches (737 $\mu$m) and an inside dimension of about 0.01 inches (about 254 $\mu$m). The precipitating solution was delivered through a tube-in-orifice within the annular orifice having an inside diameter of about 0.005 inches (about 127 $\mu$m). Precipitated fiber was quenched in a reverse osmosis water bath and taken up at a rate of 49 m/min.

Water Permeability

All fibers produced in the Examples above were evaluated for water permeability (flux) in the following manner. Water was passed through the lumens of potted test fibers with the filtering unit in a horizontal position. The ultrafiltrate port on the inlet side of the unit was plugged. Pressure monitors were placed at all inlet and outlet ports. With flow through the unit, back pressure was applied to the fiber outlet side of the unit to increase ultrafiltrate flow across the fibers. Three data points were taken at 10%, 50%, and 80–100% ultrafiltrate flow and transmembrane pressure (TMP) was calculated. Ultrafiltrate flow gas plotted against TMP and the slope of this curve was used to determine flux or water permeability. As noted above, all of the above fibers for use as water filters, hemofilters and dialyzers had water permeabilities in excess of $75\times10^{-5}$ ml/(min×cm$^2$×mmHg).

Example 8

A dialysate filter was prepared by spinning hollow fibers incorporating a polyimide. The dried fiber bundles were inserted into the molded polycarbonate case. Special potting caps were placed at the ends of the molded polycarbonate case. The ends of each fiber were cut to size. Urethane potting material was then centrifugally placed in the case to seal the fibers to the case. Excess potting material was cut away to expose the ends of the fibers and provide a fluid flow path in the completed dialysate filter. Once the ends of the filter were potted and cut, polycarbonate headers fitted with an O-ring were placed on the ends of the case. A cap was placed over the access port. One end of the filter was resealed with urethane so that the dialysate only had one outlet from the unit. The unit's maximum levels of residuals were 25 ppm for ethylene oxide, 25 ppm for ethylene chlorohydrin and 250 ppm for ethylene glycol. The unit was packaged in a sealed Tyvek pouch. The filter had the following properties:

TABLE III

| | |
|---|---|
| Fiber | Hydrophilic Polymer |
| Number of Fibers | 5000 |
| Effective Surface Area | 0.3 m$^2$ |
| Initial Pressure drop (Q = 500 ml/min) | 60 mmHg (in dialysate) |
| Maximum Pressure Drop | 160 mmHg (in dialysate) |
| Total Fluid Volume | 72 ml |
| Overall Unit Length | 192 mm |
| Unit Weight (Dry) | 145 g |
| Outer Case Material | Polycarbonate |
| Potting Compound | Polyurethane |
| O-Ring | Silicone |
| Dialysis Fluid Connectors | Hansen or Walther Connectors |

A NEO-1 Dialysate Meter from Automata Medical Instrumentation Inc. in Arizona measured conductivity upstream and downstream of the dialysate filter described above. The meter contains a flow-through conductivity cell having a temperature sensor for temperature compensation. The cell attached to the dialysate lines with Hansen®-style fittings.

Conductivity readings pre- and post the dialysate filter were stable and did not vary more than ≦2%.

Example 9

The electrolyte composition was analyzed at the filter inlet and outlet for a dialysate filter as described in Example 8. The dialysate filter was installed on a Travenol 450 SPS dialysis machine between the dialyzer-inlet and dialyzer-outlet lines. A throughput flow at 600 ml/min was initiated and concentrate uptake lines were connected to sterile, non-pyrogenic liquid bicarbonate and acid electrolyte concentrate containers. Concentrates were diluted internally by the Travenol 450 SPS using reverse osmosis water meeting the AAMI standards for water used to make dialysate.

The dialysate conductivity was allowed to stabilize as indicated by a conductivity reading taken at the filter inlet stream. We also waited until the machine issued no dialysate-related alarm conditions, including over-pressure, temperature varying from 37°±2° C. Throughput of the dialysate at 600 ml/min was continued for 30 minutes. Using a "clean-catch" technique, samples of at least 200 ml/min were collected at the filter inlet and outlet in acid washed polyethylene bottles. These bottles were sent to an outside laboratory for testing. The results of the tests were as follows:

TABLE IV

| Dialysate Analyte | Unfiltered | Filtered | ±2% VAR | Within VAriance |
|---|---|---|---|---|
| Sodium | 135 mEq/L | 133 mEq/L | 132.3–137.7 | Yes |
| Potassium | 1.9 mEq/L | 1.9 mEq/L | 1.86–1.94 | Yes |
| Chloride | 102 mEq/L | 100 mEq/L | 99.9–104.0 | Yes |
| Calcium | 6.8 mg/dl | 6.8 mg/dl | 6.6–6.94 | Yes |
| Magnesium | 1.2 mEq/L | 1.2 mEq/L | 0.000.00 | Yes |
| Aluminum | 0.099 mg/L | 0.100 mg/L | 0.097–0.101 | Yes |
| Copper | <0.002 mg/L | <0.002 mg/L | 0.00 | Yes |
| Selenium | <0.050 mg/L | <0.050 mg/L | 0.00 | Yes |
| Zinc | 0.006 mg/L | 0.006 mg/L | 0.00 | Yes |
| Chromium | <0.005 mg/L | <0.005 mg/L | 0.00 | Yes |
| Lead | <0.001 mg/L | <0.001 mg/L | 0.00 | Yes |
| Arsenic | <0.002 mg/L | <0.002 mg/L | 0.00 | Yes |
| Mercury | <0.0002 mg/L | <0.0002 mg/L | 0.00 | Yes |
| Cadmium | <0.001 mg/L | <0.001 mg/L | 0.00 | Yes |
| Fluoride | <0.10 mg/L | <0.10 mg/L | 0.00 | Yes |
| Nitrate | <0.2 mg/L | <0.2 mg/L | 0.00 | Yes |
| Sulfate | 1.0 mg/L | 1.0 mg/L | 0.00 | Yes |
| Silver | <0.003 mg/L | <0.003 mg/L | 0.00 | Yes |
| Barium | 0.002 mg/L | 0.002 mg/L | 0.00 | Yes |

**concentration variance of 2%.

Example 10

Changes to solution in terms of conductivity/resistivity and extrapolate to parts per million (or parts per billion) amounts of material contributed by a filter as described in Example 8 into the filtrate, using ultrapure de-ionized water as a filter throughput solution.

One-at-a-time, two filters were installed in a pressurized DI water line with a resistivity monitoring cell before and after the filter. The control valve was slowly opened and 1,000 ml/min flow of DI water through the filter was obtained and maintained. The inlet and outlet resistivity cell values were read and recorded at least every five minutes for a 30 minute period. The values were averaged for the two filters to arrive at a single inlet DI water resistivity value and a single outlet water resistivity value. The resistivity values were converted to ppm (or ppb) and the inlet value was subtracted from the outlet value to determine approximate ionic content added to DI water from the filter. Resistivity values were averaged over the 30 minute period and between the two filters used. Filtrate conductivity=0.169 $\mu$S/cm (or 0.37 ppm). This was an increase from the inlet DI water conductivity of 0.066 $\mu$S/cm (or 0.145 ppm). Therefore, approximately 0.224 ppm (or 224 ppb) of unknown ionic shedding or release of dissolved solids can be attributed to the filter.

TABLE V

Change in Throughput Solution Resistivity Due to Filters

| Filter # | Inlet Water Resistivity, Megohm-cm | T = 0 Minutes Filtrate Resistivity, Megohm-cm | T = 30 Minutes Filtrate Resistivity, Megohm-cm | Average Filtrate Resistivity, Megohm-cm |
|---|---|---|---|---|
| 1.00 | 15.38 | 7.00 | 5.70 | 6.25 |
| 2.00 | 14.55 | 5.63 | 5.30 | 5.48 |
| AVG | 15.10 | 6.32 | 5.50 | 5.90 |

Example 11

The filter inlet and outlet pressures (mmHg) were observed in water and final bicarbonate-based dialysate for a filter as described in Example 8. The transmembrane pressure drop was also examined as it related to the filter's effect upon the dialysate stream pressures and flow rates. A filter as described in Example 8 was installed on a Travenol 450 SPS dialysis machine between dialyzer-in and dialyzer-out dialysate lines. The sample port Tees, with 3-way stopcocks attached were installed in the upstream and downstream lines. Tubing was attached between the stopcocks and the Digi-dyne¯pressure monitor transducers (one for filter inlet pressure and one for filter outlet pressure). The stopcocks were opened to the monitoring tubing and turned on the pressure monitors.

RO water throughput at a flow at 600 ml/min was initiated. Transmembrane pressure drop was observed across the filter. The nature of the filter and whether or not the filter functioned as a flow restrictor was detected by measuring flow in the drain line with a graduated cylinder over a one minute period.

With the dialysis machine still running at 600 ml/min and monitor lines still open, dialysate throughput flow was initiated by connecting concentrate uptake lines to sterile, non-pyrogenic liquid bicarbonate and acid electrolyte concentrate containers. The acid concentrate used [were] *was* Renal Systems SB-1075 and the bicarbonate concentrate used was BC-1-L. Concentrates were diluted internally by the Travenol 450 SPS using RO water meeting the AAMI standards for water used to make dialysate.

The dialysate conductivity was allowed to stabilize as indicated by a NEO-1 Dialysate Meter reading of *the* filter inlet stream. We also waited until the machine issued no dialysate-related alarm conditions.

A throughput of 37° C., properly proportioned, bicarbonate-based, final dialysate was continued at 600 ml/min for 30 minutes. The transmembrane pressure drop across the filter was observed during dialysate throughput. Again, it was determined if the filter functioned as a flow restrictor by measuring flow in the drain line with a graduated cylinder over a one minute period.

Figure 7:
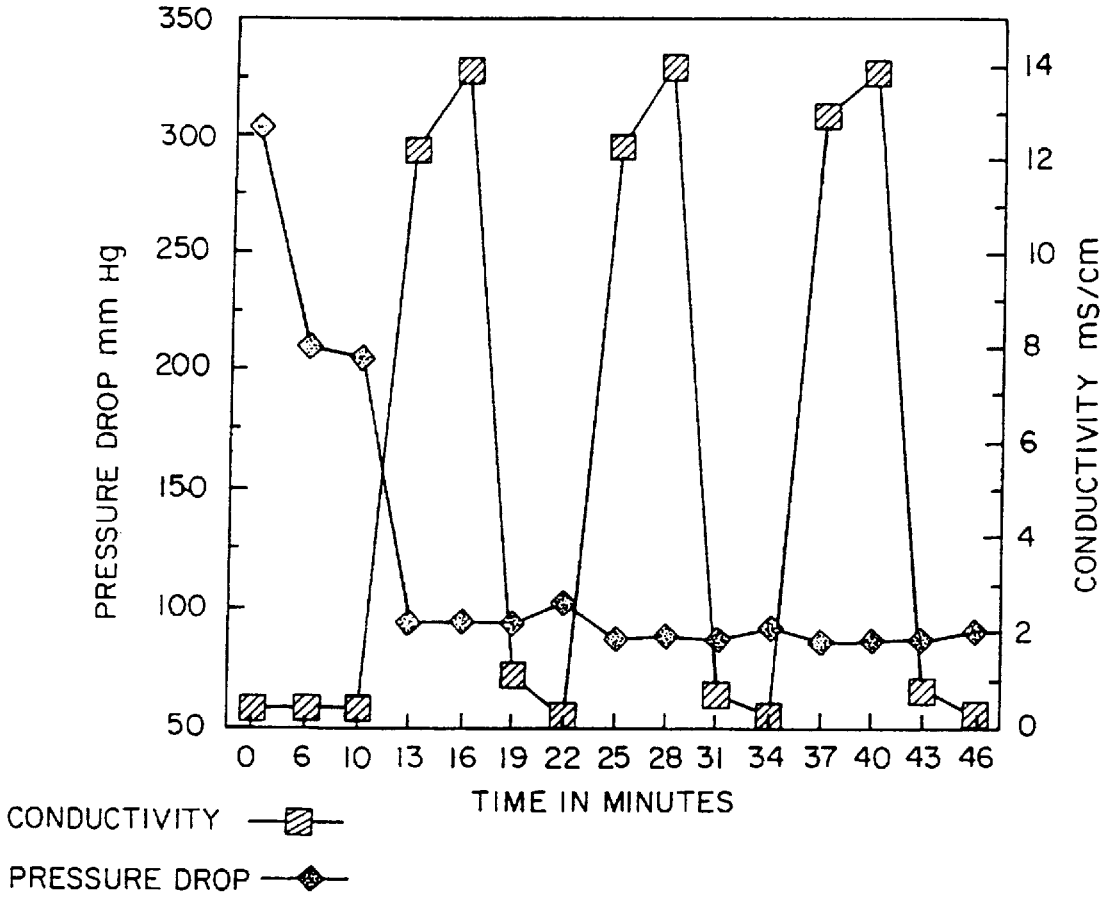
FIG. 7 illustrates the pressure drop versus conductivity for a polyimide filter.

As shown in the FIG. 7, the filter displayed a one-time variance in pressure drop that is corrected the first time each filter contacts final dialysate solution. The initial transmembrane pressure drop at 600 ml/min in RO water is about 260–340 mmHg initially. Within a few minutes, once the membrane is thoroughly "wetted", the TMP drop falls to about 200 mmHg and is stable. When contact with ion-rich dialysate occurs, the figure shows how we cycled back and forth between RO water and dialysate three times to illustrate the permanence of the change in pressure drop once dialysate contact occurs. At no time did the filter function as an actual in-line flow restrictor.

Example 12

Several different hollow fiber membrane devices were installed, one-at-a-time on a dialysis machine, under identical operating conditions, and the differences in transmembrane pressure drop in water and dialysate were determined for each device.

A filter as described in Example 8 was installed on a fully warmed up Travenol 450 SPS dialysis machine (line temperature=37°±2° C.) between dialyzer-in and dialyzer-out dialysate lines. Sample port Tees, with 3-way stopcocks attached, were installed in the upstream and downstream lines. Tubing was attached between the stopcocks and Digi-dyne® pressure monitor transducers (one for filter inlet pressure and one for filter outlet pressure). The stopcocks were opened to the monitoring tubing and the pressure monitors were turned on.

RO water throughput flow at 600 ml/min was initated and maintained for at least five minutes to allow conditions to stabilize. The flow rate was verified by measuring flow in the drain line with a graduated cylinder over a one minute period. The inlet and outlet pressures were recorded and the transmembrane pressure drop across the filter was calculated.

With the dialysis machine still running at 600 ml/min and monitor lines still open, dialysate throughput flow was initiated by connecting concentrate uptake lines to sterile, non-pyrogenic liquid bicarbonate and acid electrolyte concentrate containers. The acid concentrate used was Renal Systems® SB-1075 and the bicarbonate concentrate used was BC-1-L. Concentrates were diluted internally by the Travenol 450 SPS using RO water exceeding the AAMI standards for water used to make dialysate.

The time count began at "0" when concentrate [is] *was* hooked up to the dialysis machine. The inlet and outlet pressures were recorded and the transmembrane pressure drop across the filter was recorded every minute up to 10 minutes. The concentrate containers were then disconnected. After five minutes, a final measurement of inlet and outlet pressures was recorded and a final transmembrane pressure drop was calculated.

Steps one through five were repeated for a dialyzer using the same membrane as the RenaGuard™ Dialysate Filter (polyimide), a Minntech Primus®1350 dialyzer (polysulfone), and a Fresenius F60 dialyzer (polysulfone).

Figure 8:
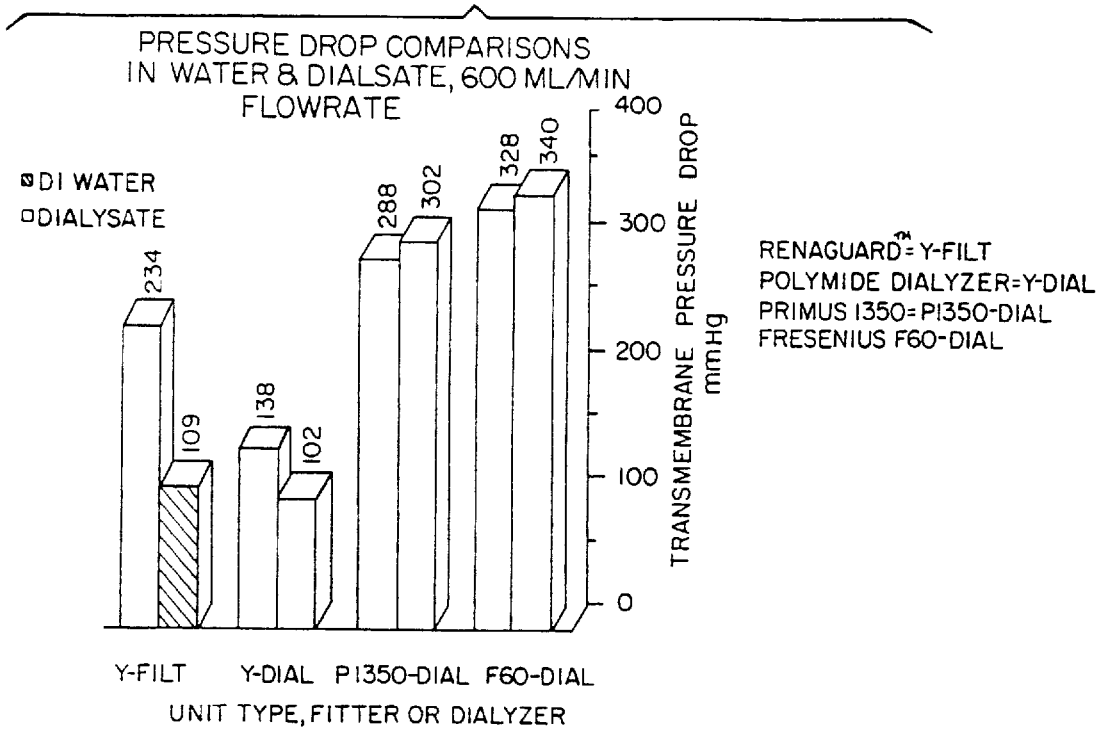
FIG. 8 illustrates a comparison of pressure drop in water for a variety of filters.

Both the RenaGuard™ Dialysate Filter and a dialyzer made with polyimide fibers had lower pressure drops than both of the Minntech and Fresenius polysulfone units. The results are set forth in FIG. 8. Polyimide fiber units had a lower pressure drop in dialysate than in RO water. The polysulfone units, on the other hand, had a higher pressure drop in dialysate.

Dialysate TMP drop measurements were done for the Fresenius F80 dialyzer and Fresenius DIASAFE hemodiafiltration unit for comparison to the RenaGuard™ Dialysate Filter in the dominant fluid environment, i.e., final dialysate.

Figure 9:
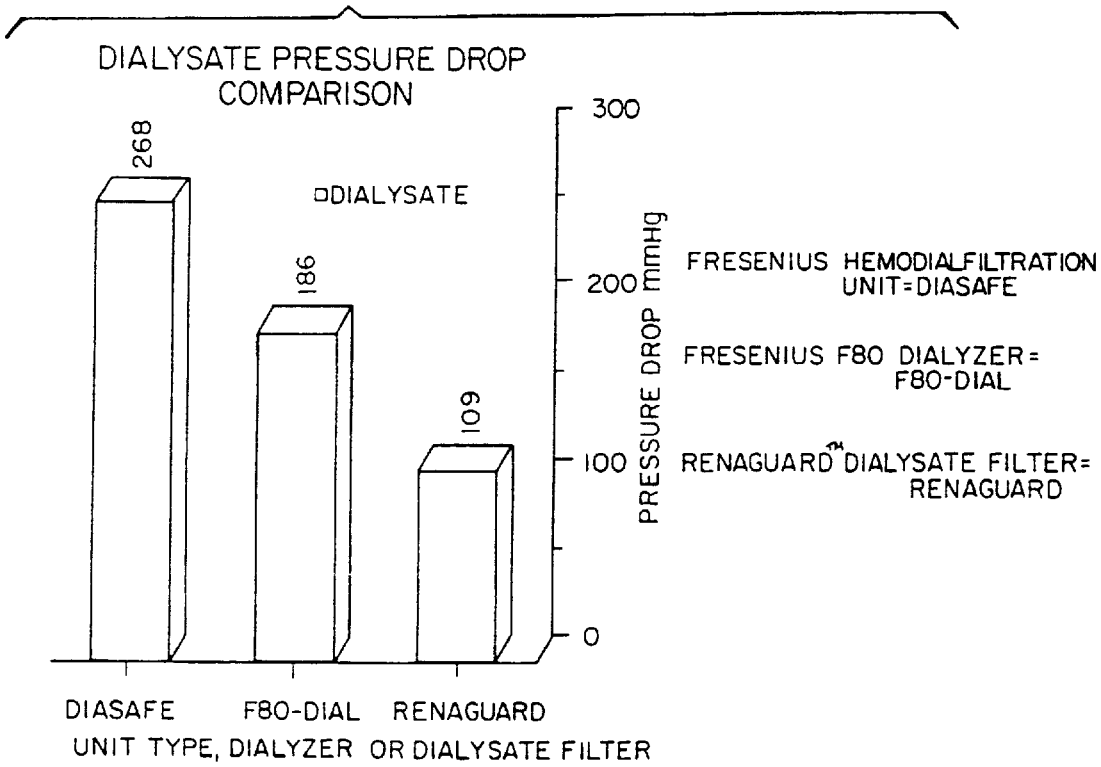
FIG. 9 illustrates a comparison of pressure drop in dialysate between polyimide containing filters and polysulfone containing filters.

The RenaGuard™ Dialysate Filter had a lower pressure drop in dialysate than either the Fresenius F80 dialyzer or the Fresenius DIASAFE hemodiafiltration filter. The results are set forth in FIG. 9.

Example 13

A "mock dialysis treatment" was set up with the dialysate filter as described in Example 8 installed immediately pre-dialyzer on a ultrafiltration-controlled (UFC) dialysis machine. The purpose of the mock dialysis treatment was to verify that the "treatment" could proceed from start to finish without alarm conditions caused by the filter, and, that the fluid removal goal for the "treatment" was within 2% of programmed goal.

Figure 1:
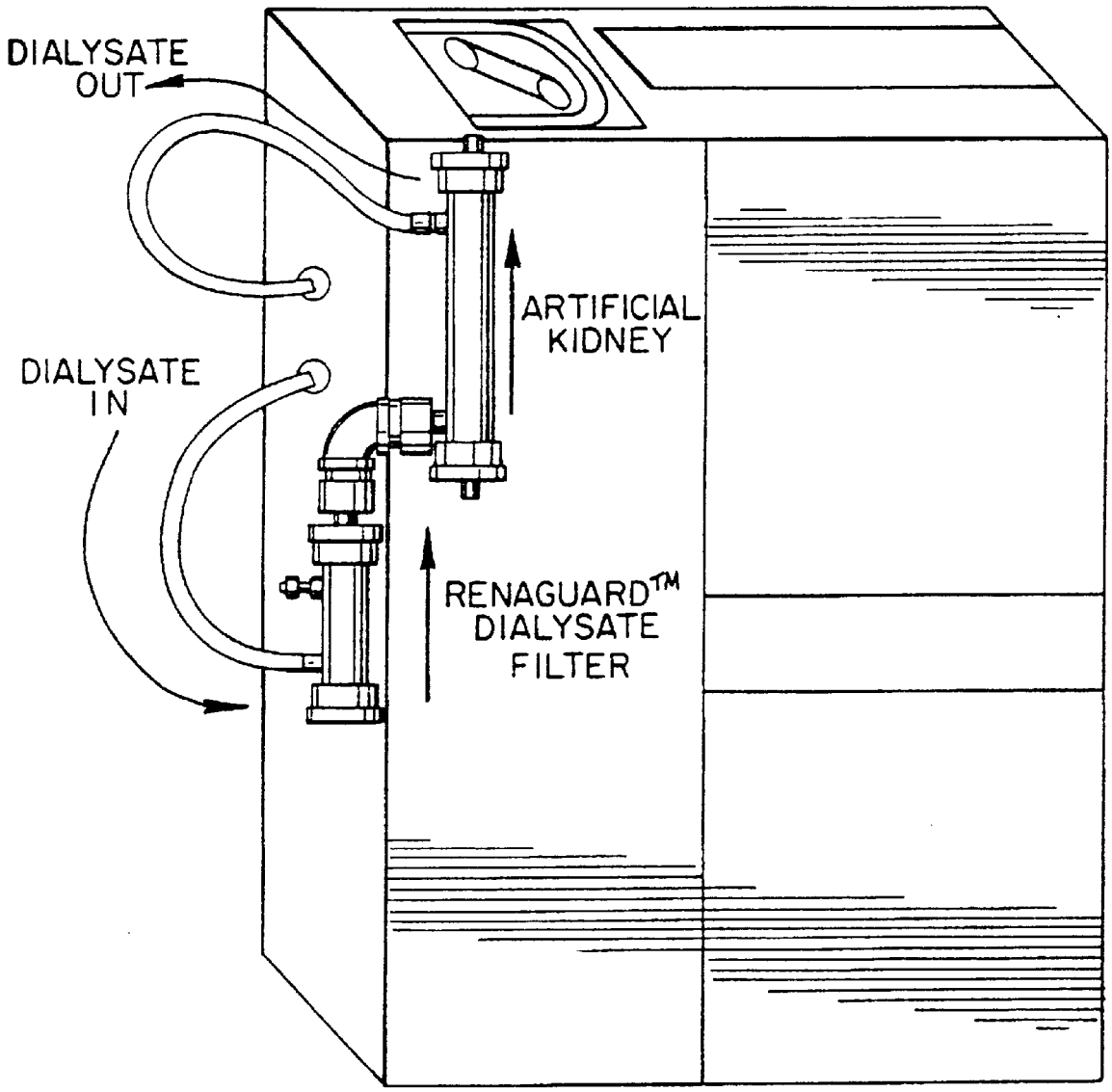
FIG. 1 depicts a dialysis apparatus with a dialysate filter of the present invention installed thereon.

A filter as described in Example 8 was installed on a Fresenius A2008H UFC dialysis machine between dialyzer-in and dialyzer-out dialysate lines. This configuration is set forth in FIG. 1.

Setup conditions included priming a Fresenius F60 dialyzer with normal saline, installing it on the A2008H machine utilizing the blood pump, pressure monitor lines, and a bucket containing saline to simulate the "patient". Blood "in" and blood "out" lines had Hoffman clamps attached to control the occlusion of the blood lines. Occlusions were set so that at a blood pump speed of 300 ml/min, the "arterial" and "venous" pressures were normalized.

Concentrates were hooked up to the machine and it was allowed to come into appropriate conductivity and temperature. At the time of "treatment", the temperature=36° C., the dialysate flow rate=500 ml/min, and the dialysate conductivity was 14.1 mS/cm.

The dialysis machine was programmed to remove 1000 ml of fluid from the "patient" in a 30 minute "treatment" time. This is the equivalent of an ultrafiltration rate of 2.0 kg/hr.

Pressures were monitored before the filter, between the filter and the dialyzer dialysate inlet, and after the dialyzer during the "treatment".

During the first "mock dialysis treatment," 1,000 ml was programmed into the A2008H to be removed from the "patient", the A2008H reported that 1,000 ml had been removed, and by collecting effluent from the ultrafiltration pump it was determined that 1,015 ml had actually been removed. This is an error of only 1.5%.

A second mock dialysis treatment was conducted with the filter inlet compartment about half full of air to determine if the reduced functional surface area would cause any "treatment" related problems. The same filter was used as in the first "treatment". The parameters were identical to those used in the first "treatment".

During the second "mock dialysis treatment" with an air-filled filter in-line, 1,000 ml was programmed into the A2008H to be removed from the "patient", the A2008H reported that 1,000 ml had been removed, and by collecting effluent from the ultrafiltration pump it was determined that 1,010 ml had actually been removed. This is an error of only 1.0%.

Example 14

In the following example, filters as described in Example 8 were used with a dialysate throughput of 20,000 liters.

Two dialysate filters were installed on a test bench containing a 50-liter container of correctly proportioned bicarbonate-based dialysate. Using Tygon tubing segments and appropriate connectors, each filter was connected to a roller pump that drew dialysate out of the container, pushed it through the filter, and returned dialysate filtrate back into the container at a constant flow rate of 800 ml/min.

This test simulated the use of greater than one month's worth of poor-quality dialysate at a higher than usual throughput flow rate. Dialysate flow rates can vary from 500–1,000 ml/min, however, typically they do not exceed 600 ml/min. Bacterial load in the 50-liter container varied from 10 cfu/ml at the start of the study to 300 cfu/ml at the end of the study.

Post-filter samples for each filter and the 50-liter container were sampled periodically during the test and after 18 days of dialysate recirculation and throughput. Collection of dialysate container samples was accomplished by using a sterile 25 ml pipette to transfer at least 100 ml of dialysate from the container into a sterile collection bottle. Collection of post-filter samples was accomplished by using a "clean catch" method. The downstream tubing connector was removed from the filter and dialysate was allowed to run out of the outlet port for about 5 seconds. A sterile collection bottle was placed under the stream and at least 100 ml of solution was collected.

Collection bottle contents were filtered through a 0.2 [um] *μm* Nalgene disposable filter. Sterile forceps were used to transfer the membrane portion [df] *of* the filter onto Tryptic soy agar (TSA) for determination of cfu/ml. TSA Plates were incubated at 37° C. for 48 hours.

At the 20,000 liters throughput level, 48 hour plates showed "no growth" for the outlet samples of both filters. Shortly after the start of the study, the dialysate container sample showed about 300 cfu/ml of bacteria within the dialysate solution entering the dialysate filter inlets.

Example 15

A single filter as described in Example 8 was removed from its package and installed on a Travenol 450 SPS dialysis machine, between the lines normally used as dialysate-inflow and dialysate-outflow for the dialysate compartment on a hemodialyzer during dialysis. Properly proportioned bicarbonate-based 37° C. dialysate throughput was initiated and maintained at 600 ml/min.

Prior to installation of the dialysate filter, the Travenol machine had been treated with 250 ml of Renalin® Concentrate diluted within the dialysis machine 1:8 in RO water and allowed to dwell within the machine for 30 minutes. After this time, the machine was allowed to rinse until peracetic acid test strips indicated <1 ppm in the drain line. Peroxide levels from the Renalin® were also verified <1 ppm in filter outlet samples as detected by using a Spectrophotometer.

A bacterial suspension of Escherichia coli, grown on TSA and diluted with 25 ml of bicarbonate dialysate, was added to the bicarb concentrate jug to "spike" the final dialysate entering the dialysate filter. The Travenol machine was hooked up to this "contaminated" bicarbonate concentrate and allowed to proportion per normal functioning. This resulted in a bacterial challenge level of at least $1.6\times10^7$ cfu/ml.

Samples of at least 100 ml were collected from pre- and post-filter sample ports using "clean catch" technique at T=0, 5, 30, and 60 minutes. Samples were filtered through a 0.2 μm Nalgene disposable filter. Sterile forceps were used to transfer the membrane portion of the filter onto Tryptic soy agar (TSA) for determination of cfu/ml. TSA Plates were incubated at 37° C. for 48 hours.

Environmental and media controls were negative. Positive control was positive for growth. All culture results are reported in cfu/ml after 48 hours incubation at 37° C. Note in the Table below that all filtrate samples were negative.

TABLE VI

| Sample | cfu/ml |
|---|---|
| T = 0 Pre-filter | 1 |
| T = 0 Post-filter | 0 |
| T = 0 Bicarb jug | $1.8 \times 10^7$ |
| T = 5 Pre-filter | $1.6 \times 10^7$ |
| T = 5 Post-filter | 0 |
| T = 30 Pre-filter | $1.9 \times 10^7$ |
| T = 30 Post-filter | 0 |
| T = 60 Pre-filter | $1.9 \times 10^7$ |
| T = 60 Post-filter | 0 |

Example 16

Two dialysate filters as described in Example 8 were installed on separate Travenol 450 SPS dialysis machines and left attached between the dialysate-inflow and dialysate-outflow lines. Each filter was exposed to over 600 liters of throughput, 500 liters of which were properly proportioned final bicarbonate-based dialysate, the remainder being RO water. The throughput flow rate was 600 ml/min.

One filter was challenged with Escherichia coli bacteria in dialysate after two days; the other filter was similarly challenged after three days of installation. As in Example 15, a bacterial suspension of Escherichia coli; grown on TSA and diluted with 25 ml of bicarbonate dialysate, was added to the bicarb concentrate jug to "spike" the final dialysate entering the dialysate filter. The Travenol machine was hooked up to this "contaminated" bicarbonate concentrate and allowed to proportion per normal functioning. This resulted in a bacterial challenge level of at least $3.6 \times 10^4$ cfu/ml.

Prior to initiating the bacterial challenge, each Travenol machine had been treated with 250 ml of Renalin® Concentrate diluted within the dialysis machine 1:8 in RO water and allowed to dwell within the machine for 30 minutes. After this time, the machine was allowed to rinse until peracetic acid test strips indicated <1 ppm in the drain line. Peroxide levels from the Renalin® were also verified <1 ppm in filter outlet samples as detected by using a Spectrophotometer.

Once the contaminated bicarb jug was hooked up to the Travenol machine, samples of at least 100 ml were collected from pre- and post-filter sample ports using "clean catch" technique at T=0, 5, 30, and 60 minutes. Samples were filtered through a 0.2 [um] $\mu m$ Nalgene disposable filter. Sterile forceps were used to transfer the membrane portion of the filter onto Tryptic soy agar (TSA) for determination of cfu/ml. TSA Plates were incubated at 37° C. for 48 hours.

Environmental and media controls were negative. Positive control was positive for growth. All culture results are reported in cfu/ml after 48 hours incubation at 37° C.

TABLE VII

Filter #1, After 2 days

| Sample | cfu/ml |
|---|---|
| T = 0 Pre-filter | 147 |
| T = 0 Post-filter | 2 |
| T = 0 Bicarb jug | $1.5 \times 10^6$ |
| T = 5 Pre-filter | $2.5 \times 10^5$ |
| T = 5 Post-filter | 0 |
| T = 30 Pre-filter | $2.1 \times 10^5$ |
| T = 30 Post-filter | 0 |

TABLE VII-continued

Filter #1, After 2 days

| Sample | cfu/ml |
|---|---|
| T = 60 Pre-filter | $2.2 \times 10^5$ |
| T = 60 Post-filter | 1 |

TABLE VIII

Filter #2, After 3 days

| Sample | cfu/ml |
|---|---|
| T = 0 Pre-filter | 319 |
| T = 0 Post-filter | 0 |
| T = 0 Bicarb jug | $4.7 \times 10^5$ |
| T = 5 Pre-filter | $3.6 \times 10^4$ |
| T = 5 Post-filter | 33 |
| T = 30 Pre-filter | $4.7 \times 10^4$ |
| T = 30 Post-filter | 1 |
| T = 60 Pre-filter | $3.7 \times 10^4$ |
| T = 60 Post-filter | 1 |

Example 17

Eight (8) ETO'd dialysate filters as described in Example 8, were challenged to verify retention of Pseudomonas aeruginosa endotoxin in final dialysate at flowrates of 500–1,000 ml/min.

Eight filters were installed in the test setup for one-at-a-time evaluation. For seven of these filters, this setup consisted of inlet and outlet tubing with Hansen-style connectors for each filter's inlet and outlet ports, a roller pump, an inlet and outlet sampling port installed pre- and post-filter and clean pyrogen-free 2½ gallon polyethylene jugs (containers for the rinsing and challenging solutions). One filter, however, was installed on a Travenol 450 SPS dialysis machine, between the dialyzer inlet and dialyzer outlet lines-connected in the same way a dialyzer's dialysate ports would be during a hemodialysis treatment.

Filters were "rinsed" with final bicarbonate-based dialysate solution at 500 ml/min for 30 minutes before being "challenged" with contaminated dialysate (containing the Pseudomonas aeruginosa endotoxin).

Frozen, dried lipopolysaccharide (LPS, endotoxin), isolated from Pseudomonas aeruginosa by phenol extraction was reconstituted per the manufacturer's instructions and added to the final bicarbonate-based dialysate solution immediately prior to initiating the test. The 2½ gallon container was vigorously shaken and then placed on a magnetic stirring platform, with a stirring bar in the bottom, to help keep the solution mixed.

Prior to starting the test, the pre- and post-filter ports, with no filter in-line, were sampled to verify pyrogen-free status. Ports were checked again, with filter in-line, before administering the endotoxin challenge to verify that the filter was clean and that the test setup did not become contaminated during the installation of the filter.

Once the flow of contaminated dialysate was initiated through the filter, samples were collected from the pre- and post-filter sample ports at T=1, 3, and 5 minutes.

The gel-clot method of Limulus Amebocyte Lysate endotoxin assaying was used to analyze all samples for presence, absence, or quantification of endotoxin. Additional test conditions included the following:

a. One filter was challenged in both DI water and dialysate. This filter received two back-to-back endotoxin challenge tests.

b. Two filters were challenged with LPS that had been sonicated in addition to vortexing.

c. One filter was challenged with a throughput flowrate=800 ml/min instead of 500 ml/min.

d. One filter was challenged with a throughput flowrate=1,000 ml/min in addition to the 500 ml/min rate. This filter also received two back-to-back endotoxin challenge tests.

e. One filter had been "pre-treated" by installing it as a pre-filter for the Renatron® artificial kidney reprocessing machine. It was exposed to RO water throughput conditions of up to 6.2 liters/min (6,200 ml/min) during ten (10) Renatron® processing cycles.

f. Again, one filter was installed on a dialysis machine as described above and exposed to throughput flowrates of 600 ml/min. This dialysis machine picked up the endotoxin contamination from the water inlet to the machine, instead of from contaminated dialysate. Frozen, dried Pseudomonas aeruginosa LPS, was reconstituted per the manufacturer's instructions and added to the water supply for the dialysis machine (a 50-liter polyethylene container). To provide adequate pressure for dialysis machine operation, a roller pump "pushed" the contaminated water stream into the dialysis machine.

Filters received endotoxin challenges varying in potency from 4.8 EU/ml up to 60 EU/ml of Pseudomonas aeruginosa endotoxin at final bicarbonate-based dialysate throughput flowrates of 500 ml/min, 800 ml/min, or 1,000 ml/min. Each of the filters retained all endotoxin. No detectable endotoxin is reported as <0.06 EU/ml, the limit of sensitivity for the Lysate used in the assay.

TABLE IX

*Pseudomonas aeruginosa* Dialysate Endotoxin Challenge

| Filter # | Endotoxin Challenge Level, EU/ml | Endotoxin Filtrate Level, EU/ml 1 MIN | 3 MIN | 5 MIN | Treatment conditions |
|---|---|---|---|---|---|
| 1 | 6 | <0.06 | <0.06 | <0.06 | Also DI water, 48 EU/ml in, <0.06 EU/ml in all outlet samples |
| 2 | 6 | <0.06 | <0.06 | <0.06 | — |
| 3 | 12 | <0.06 | <0.06 | <0.06 | Pseudomonas LPS sonicated & vortexed prior to use |
| 4 | 60 | <0.06 | <0.06 | <0.06 | Pseudomonas LPS sonicated & vortexed prior to use |
| 5 | 12 | <0.06 | <0.06 | <0.06 | 800 ml/min throughput flowrate |
| 6 | 24 | <0.06 | <0.06 | <0.06 | Run on dialysis machine, 600 ml/min LPS introduced into water inlet |
| 7 | 4.8 | <0.06 | <0.06 | <0.06 | Pre-treated with 10 Renatron ® cycles |
| 8 | 6 | <0.06 | <0.06 | <0.06 | Also 1,000 ml/min throughput flowrate, 12 EU/ml inlet, <0.06 EU/ml outlets |

Example 18

Six (6) ETO'd filters as described in Example 8 were challenged with endotoxin in RO water at flowrates of 2,000 ml/min and verify endotoxin retention.

Six filters were individually removed from the Tyvek bag used during the ETO sterilization process and installed in the test setup for one-at-a-time evaluation. RO water was used as the challenge solution due to the difficulty presented in producing large volumes of clean dialysate to support the 2 liters per minute flow rate used in this test.

The test setup used in Example 17 was also used for this test series. The most noteworthy differences between Example 17 and this example include the following:

a. RO water was used instead of final bicarbonate-based dialysate.

b. Throughput flowrate=2,000 ml/min instead of the 500–1,000 ml/min used in Example 17.

c. The first two filters were challenged using endotoxin derived from Escherichia coli. The last four were challenged with Pseudomonas aeruginosa LPS.

d. The last five filters tested had LPS delivered into the dialysate by using a metered syringe pump with a glass syringe. The concentrated, reconstituted LPS was drawn up into the syringe and a line attached to the filter inlet tubing. The syringe pump injected endotoxin at a controlled rate from the syringe directly into the filter inlet stream.

Prior to starting the test, pre- and post-filter ports, with no filter in-line, were sampled to verify pyrogen-free status of the test setup. Ports were checked again, with filter in-line, before administering the endotoxin challenge to verify that the filter was clean and that the test setup did not become contaminated during the installation of the filter.

Samples were collected from filter inlet and outlet sample ports at T=1 and T=4 minutes after LPS administration was initiated. Once the 4 minute samples were collected, with the syringe pump still "on" the filter was removed and filter inlet and outlet ports were sampled again to verify that endotoxin was present in both ports, showing that reduced endotoxin concentrations were not caused by some artifact in the test setup.

Again, the gel-clot method of Limulus Amebocyte Lysate endotoxin assaying was used to analyze all samples for presence, absence, or quantification of endotoxin. To simplify the testing process, a "Pass/Fail Limits Test" was used. Rather than perform an extensive dilution series to determine the exact concentration of endotoxin present in the contaminated dialysate, a single appropriately diluted sample was used, which if positive, indicated the minimum level of endotoxin present, e.g., ≧15 EU/ml.

Filters received endotoxin challenges varying in potency from ≧15 EU/ml up to 48 EU/ml; of either Escherichia coli or Pseudomonas aeruginosa endotoxin at RO water throughput flowrates of 2,000 ml/min. Each filter retained all endotoxin contained within the challenge solution. No detectable endotoxin is reported as <0.06 EU/ml, the limit of sensitivity for the Lysate used in the assay. (See Table below for details.)

TABLE X

Syringe Pump Endotoxin Challenge at 2,000 ml/min

| Filter # | Endotoxin Challenge Level, EU/ml | Endotoxin Filtrate Level, EU/ml 1 MIN | 4 MIN | Treatment conditions |
|---|---|---|---|---|
| 1 | 48 | <0.06 | <0.06 | *E. Coli* LPS, contaminated RO water in 2½ gallon jug |
| 2 | 24 | <0.06 | <0.06 | *E. Coli* LPS, Syringe pump administration |
| 3 | ≧15 | <0.06 | <0.06 | *P. aeruginosa* LPS, Syringe pump administration |
| 4 | ≧15 | <0.06 | <0.06 | *P. aeruginosa* LPS, Syringe pump administration |
| 5 | ≧15 | <0.06 | <0.06 | *P. aeruginosa* LPS, Syringe pump administratoin |
| 6 | ≧15 | <0.06 | <0.06 | *P. aeruginosa* LPS, Syringe pump administration |

Example 19

To evaluate reusability of the filters of the present invention as described in Example 8, four (4) filters that demonstrated "shedding" of LAL-reactive material were treated with Renalin® Concentrate to recover their endotoxin retention capability.

To produce this condition in which filters release or "shed" LAL-reactive material, filters were run 24 hours/day on a recirculation setup with contaminated dialysate. Shedding only occurs in filters that have not been periodically re-sterilized during use (every 24–48 hours).

This "recirculation" setup included a 50-liter container of final bicarbonate-based dialysate, a roller pump, and connecting tubing with Hansen-style connectors for attachment to filter [in-lets] *inlets* and outlets. The roller pump moved dialysate up to the pump, through the filters, and returned the dialysate filtrate back into the 50-liter container. This setup provided throughput of 800 ml/min, 24 hours/day for each filter. The dialysate was deliberately not disinfected so that levels of bacteria in the tank would rise over time.

Before the re-evaluation of endotoxin retention was conducted, all four units were pre-treated on the "recirculation" setup until they began to "shed" LAL-reactive material into throughput solutions. "Shedding" was verified using gel-clot LAL assays of filtrate samples.

We had observed, that at a point between 10,000 liters and 20,000 liters total dialysate throughput, the filters began "shedding" of LAL-reactive material into the filtrate. Concurrently, the pressure drop across the filters had doubled. That is, they showed less permeability to throughput fluids, and no longer served to depyrogenate the fluids flowing through them. When pyrogen-free RO water was input to the filter the fluid became LAL-reactive.

To evaluate the "recoverability" of these "saturated" filters, a method was devised to disinfect and clear the membrane of this LAL-reactive material. It was hypothesized that this material consisted of accumulated bacteria and endotoxin, precipitated salts and carbonates, and by-products of bacterial metabolism resulting from some kind of "growthrough" phenomenon. Note that the filters had not been disinfected or re-sterilized during the entire time of their installation in the recirculating setup.

The membrane disinfection and clearing procedure consisted of the following steps:

a. Removing the filter from the recirculating setup.

b. Installing it in reverse configuration (to "blow off" the material impacted on the membrane surface) on a Travenol 450 SPS dialysis machine, in between the dialysate in-flow and out-flow lines.

c. Running RO water through the filter at 600 ml/min during a Renalin® Concentrate chemical treatment on the dialysis machine.

1) Allowing the dialysis machine to draw up 250 ml of Renalin® Concentrate through the acid concentrate uptake line (resulting in a 1:8 dilution of Renalin® Concentrate in the filter and machine dialysate lines).

2) Turning off the dialysis machine and allowing the diluted Renalin® Concentrate to dwell inside the filter for 30 minutes.

3) Turning on the dialysis machine and "rinsing" the filter with RO water until <1 ppm of Renalin® was detected. This took about 20 minutes to accomplish.

d. Re-orienting the filter to normal flow direction and installing it on the endotoxin challenge test bench.

All four filters ran on the recirculating test setup until they began to "shed" LAL-reactive material. They were then given the Renalin® membrane clearing and disinfecting treatment described above and installed on the endotoxin challenge test bench in preparation for the post-treatment LPS retention test.

This endotoxin test setup consisted of a roller pump, inlet and outlet tubing and Hansen-style connectors, pre- and post-filter sampling ports, and 2½ gallon polyethylene containers for holding the challenge solutions. All tests used DI water throughput at a flowrate=500 ml/min.

Again, the gel-clot method of Limulus Amebocyte Lysate endotoxin assaying was used to analyze all samples for presence, absence, or quantification of endotoxin.

Prior to starting the test, the pre- and post-filter ports, with no filter in-line, were sampled to verify non-pyrogenic status. Ports were checked again, with filter in-line, before administering the endotoxin challenge to verify that the filter was clean and that the test setup did not become contaminated during the installation of the filter.

Frozen, dried lipopolysaccharide (LPS, endotoxin), isolated from Escherichia coli by phenol extraction, was reconstituted per the manufacturer's instructions and added to a 2½ gallon container of pyrogen-free RO water immediately prior to initiating the test. The 2½ gallon container was vigorously shaken and then placed on a magnetic stirring platform, with a stirring bar in the bottom, to help keep the solution mixed.

Once the LPS contamination was initiated, samples were collected from filter inlet and outlet sample ports at T=1, 3, and 5 minutes.

Filters were exposed to recirculating dialysate throughput flowrates of 800 ml/min, 24 hours/day until the transmembrane pressure drop had doubled. Within this highly exaggerated test condition, the filters began to "shed" LAL-reactive material. Filters were then subjected to a Renalin® membrane clearing and disinfecting procedure.

Filters then received follow-up endotoxin challenges varying in potency from ≧7.7 EU/ml up to 30.7 EU/ml of Escherichia coli endotoxin at RO water throughput flowrates of 500 ml/min. Each filter retained all endotoxin contained within the challenge solution. No detectable endotoxin was reported as <0.06 EU/ml, the limit of sensitivity for the Lysate used in the assay. (See Table below for details.)

TABLE XI

Recovery of Endotoxin Retention After Renalin ® Exposure

| Filter # | Treatment conditions | "Shedding" LAL-reactive Material before Renalin ® Treatment ? (Y/N) | Endotoxin Challenge Level, EU/Ml (After Renalin ®) | Endotoxin Filtrate Level, EU/ml 1 MIN | 3 MIN | 5 MIN |
|---|---|---|---|---|---|---|
| 1 | 20,000 liters recirculated dialysate, then Renalin ®-treated | Yes, >0.06 EU/Ml | 15.4 | <0.06 | <0.06 | <0.06 |
| 2 | 20,000 liters recirculated dialysate, then Renalin ®-treated | Yes, >0.06 EU/Ml | 15.4 | <0.06 | <0.06 | <0.06 |
| 3 | 20,000 liters recirculated dialysate, then Renalin ®-treated | Yes, >0.06 EU/Ml | 7.7 | <0.06 | <0.06 | <0.06 |
| 4 | 20,000 liters recirculated dialysate, then Renalin ®-treated | Yes, >0.06 EU/Ml | 30.7 | <0.06 | <0.06 | <0.06 |

Example 20

The outlet header cap of a filter as described in Example 8 was contaminated with 0.1 ml of a $10^{10}$ cfu/ml suspension Bacillus subtilis spores, 25 ml of Renalin® Cold Sterilant Concentrate was then injected into the filter for a 12 hour dwell period and viability of the spores was checked.

A dialysate filter, representative of final sterilized product, was installed on a Travenol 450 SPS dialysis machine between the dialyzer-in and dialyzer-out dialysate lines. Flow was initiated through the filter at 600 ml/min and the machine was connected to bicarbonate and acid electrolyte solutions. The machine was allowed to proportion final dialysate until 37° C. temperature and 13.8 mS/cm solution conductivity was obtained (normal final dialysate parameters).

The dialysis machine was turned off and 25 ml of Renalin® Cold Sterilant Concentrate was injected into the Luer port provided on the filter. The outlet header coupler was then disconnected and 0.1 ml of a $10^{10}$ cfu/ml Bacillus subtilis bacterial endospore suspension was pipetted into the header cap.

The filter was left installed in the dialysate lines on the dialysis machine, with the Renalin® dwelling for about 16 hours.

After the dwell period, the filter unit was removed from the dialysis machine and the fluid it contained was drained into a sterile collection bottle. It was then re-attached to the dialysis machine and the machine turned on to flush another 100 ml out through the unit. The end volume in the collection bottle was about 200 ml.

This 200 ml of effluent solution was aseptically filtered through a 0.2 $\mu$m membrane filter. It was then rinsed with 90 ml of 1% peptone/1% sodium thiosulfate solution to neutralize the Renalin®, followed by 100 ml sterile DI water.

The effectiveness of this 90 ml 1% peptone/1% sodium thiosulfate neutralizing "rinse" procedure was verified. By contaminating the 100 ml sterile DI water used as a rinse (above) with Bacillus subtilis spores, plating the 0.2 $\mu$m filter on TSA, and incubating at 37° C. for 24 hours, we were able to show bacterial growth. This indicates effective neutralization of the Renalin® used in the test.

After 48 hours incubation at 37° C., one colony grew on the 0.2 $\mu$m membrane filter. This colony had a similar morphology to the inoculated organism (Bacillus subtilis). To confirm the presence of the inoculated organism, a Gram stain was done on the colony. The results of the Gram stain showed gram positive cocci instead of the Gram negative bacilli sporeformer. This suggests that the single colony was the result of some type of contamination during either preparation or collection.

Example 21

To further evaluate the disinfection effectiveness of a 6 to 12 hour dwell period, a suspension containing $10^{10}$ Bacillus subtilis bacterial endospores were injected into the fluid inlet stream of four filters as described in Example 8, driving the spores against the filter membrane. Inject 10–25 ml of Renalin® Cold Sterilant Concentrate into each filter, and check viability of spores after six to twelve hours.

First a test was conducted to demonstrate the recoverability of Bacillus subtilis spores impacted upon the dialysate filter membrane. An ETO-sterilized dialysate filter was installed on a Travenol 450 SPS dialysis machine between the dialyzer-in and dialyzer-out dialysate lines. RO water flow was initiated through the filter at 600 ml/min. One ml of about $10^{10}$ Bacillus subtilis spores [were] *was* injected into the filter's inlet stream. The dialysis machine was allowed to run for about 5 more minutes. Then, by reversing the filter's installation configuration we were able to "blow off" the spores embedded or impacted upon the membrane. Recovery was estimated to be nearly 100%.

Then, each of the four filters to be used in the sporicidal Renalin® treatment test was installed one-at-a-time on a Travenol 450 SPS dialysis machine between the dialyzer-in and dialyzer-out dialysate lines. RO water flow was initiated through each filter at 600 ml/min. One ml containing $10^{10}$ spores was injected into the filter's inlet stream and the machine was allowed to run for another 5 minutes to drive the spores against the membrane. The machine was turned off and 10 ml of Renalin® Concentrate was injected into the Luer port on each filter. The filters remained installed on the dialysis machine for a minimum of six hours.

This 10 ml of Renalin® Cold Sterilant Concentrate, injected into the 85 ml fluid volume of the filter, yields an effective Renalin® concentration of $\geqq$1% (about 2.8% hydrogen peroxide within the filter).

After the dwell period, the flow through each filter was reversed by disconnecting the two dialysate lines and reconnecting the "upstream" line to the "downstream" port. The dialysis machine was turned on and throughput flow initiated at 600 ml/min for about 30 seconds. Filtrate was collected (about 300 ml) in a sterile collection bottle.

Filtrate was then passed through a sterile 0.2 $\mu$m Nalgene analytical filter, followed by at least 90 ml of the "neutralizing rinse" used in the previous test. The neutralizing rinse was then followed by at least 100 ml of sterile DI water.

The analytical membrane filter was then moved with a sterile forceps onto a TSA plate and allowed to incubate for at least 48 hours at 37° C. If any growth was present, a Gram stain was done to help determine if the colony was the same as the inoculating [organis] *organism* (Bacillus Subtilis).

After 48–72 hours incubation at 37° C., filter#1's test solution had one colony forming unit. A Gram stain was done on the colony and it was found to be Gram positive Staphylococci, not the inoculating organism. This is probably due to contamination during setup or collection. Therefore, in the Table below, the result was recorded as "no growth". The other three filters' test solutions were all negative for any growth.

TABLE XII

| Filter # | Number of Spores Injected Total | Renalin ® Used, ml | Dwell Time, hours | Incubation Period, hours | Post-Treatment Spores Viable, cfu/ml |
|---|---|---|---|---|---|
| 1 | 10 Billion | 25 | 12 | 48 | 0 |
| 2 | 10 Billion | 20 | 6 | 72 | 0 |
| 3 | 10 Billion | 10 | 6.5 | 48 | 0 |
| 4 | 10 Billion | 10 | 6 | 48 | 0 |

Example 22

The outlet header cap of a filter as described in Example 8 was contaminated with 0.1 ml of a $10^{10}$ cfu/ml suspension Bacillus subtilis spores, and then injected with 25 ml of Renalin® Cold Sterilant Concentrate to check the viability of spores after twelve (12) hours.

An ETO'd dialysate filter was installed on a Travenol 450 SPS dialysis machine between the dialyzer-in and dialyzer-out dialysate lines. Flow was initiated through the filter at 600 ml/min and the machine was connected to bicarbonate and acid electrolyte solutions. The machine was allowed to proportion final dialysate until 37° C. temperature and 13.8 mS/cm solution conductivity was obtained (normal final dialysate parameters).

The dialysis machine was turned off and 25 ml of Renalin® Cold Sterilant Concentrate was injected into the Luer port provided on the filter. The outlet header coupler was then disconnected and 0.1 ml of a $10^{10}$ cfu/ml Bacillus subtilis bacterial endospore suspension was pipetted into the header cap.

The filter was left installed in the dialysate lines on the dialysis machine, with the Renalin® indwelling for about 12 hours.

After the dwell period, the filter unit was removed from the dialysis machine and the fluid it contained was drained into a sterile collection bottle. It was then re-attached to the dialysis machine and the machine turned on to flush another 100 ml out through the unit. The end volume in the collection bottle was about 200 ml.

This 200 ml of effluent solution was aseptically filtered through a 0.2 $\mu$m membrane filter. It was then rinsed with 90 ml of 1% peptone/1% sodium thiosulfate solution to neutralize the Renalin®, followed by 100 ml sterile DI water.

The effectiveness of this 90 ml 1% peptone/1% sodium thiosulfate neutralizing "rinse" was verified. By contaminating the 100 ml sterile [D1] *DI* water used as a rinse (above) with Bacillus subtilis spores, plating the 0.2 $\mu$m filter on TSA, and incubating at 37° C. for 24 hours, we were able to show bacterial growth. This indicates effective neutralization of the Renalin® used in the test.

After 48 hours incubation at 37° C., one colony grew on the 0.2 $\mu$m membrane filter. This colony had a similar morphology to the inoculated organism (Bacillus subtilis). To confirm the presence of the inoculated organism, a Gram stain was done on the colony. The results of the Gram stain showed gram positive cocci instead of the Gram negative bacilli sporeformer. This suggests that the single colony was the result of some type of contamination during either collection or filtration and not due to resistance to Renalin®. [Result] *The result was* recorded as "no growth".

Example 23

Four (4) prototype RenaGuard® Dialysate Filters, were injected with a suspension containing $10^{10}$ Bacillus subtilis bacterial endospores into each filter's fluid inlet stream, driving them against the filter membrane. 10–25 ml of Renalin® Cold Sterilant Concentrate was injected into the filter, and the viability of the spores was checked after six to twelve hours.

We decided that contamination of the dialysate filter should occur in the same manner it would clinically. That is, the bioburden (bacteria and endotoxin) would impact on the outside of the membrane due to the filter's normal throughput flow direction.

We first conducted a test to demonstrate the recoverability of Bacillus subtilis spores as it impacted upon the dialysate filter membrane. An ETO'd dialysate filter was installed on a Travenol 450 SPS dialysis machine between the dialyzer-in and dialyzer-out dialysate lines. RO water flow was initiated through the filter at 600 ml/min. One ml of about $10^{10}$ cfu/ml Bacillus subtilis spores [were] *was* injected into the filter's inlet stream. The dialysis machine was allowed to run for about 5 more minutes. Then, by reversing the filter's installation configuration we were able to "blow off" the spores embedded or impacted upon the membrane. Recovery was estimated to be nearly 100%.

Then, each of the four filters to be used in the sporicidal Renalin® treatment test was installed one-at-a-time on a Travenol 450 SPS dialysis machine between the dialyzer-in and dialyzer-out dialysate lines. RO water flow was initiated through each filter at 600 ml/min. One ml of spore suspension was injected into the filter's inlet stream and the machine was allowed to run for another 5 minutes to drive the spores against the membrane. The machine was turned off and Renalin® Concentrate was injected into the Luer port on each filter. The filters remained installed on the dialysis machine for a minimum of six hours with Renalin® indwelling.

After the dwell period, the flow through each filter was reversed by disconnecting the two dialysate lines and reconnecting the "upstream" line to the "downstream" port. The dialysis machine was turned on and throughput flow initiated at 600 ml/min for about 30 seconds. Filtrate was collected (about 300 ml) in a sterile collection bottle.

Filtrate was then passed through a sterile 0.2 $\mu$m Nalgene analytical filter, followed by at least 90 ml of the "neutralizing rinse" used in the previous test. The neutralizing rinse was then followed by at least 100 ml of sterile DI water.

The analytical membrane filter was then moved with a sterile forceps onto a TSA plate and allowed to incubate for at least 48 hours at 37° C. If any growth was present, a Gram stain was done to help determine if the colony was the same as the inoculating organism (Bacillus subtilis).

After 48–72 hours incubation at 37° C., filter#1's test solution had one colony growing. A Gram stain was done on the colony and it was found to be Gram positive Staphylococci, not the inoculating organism. [Result] *The result was* recorded as "no growth". The other three filters' test solutions were all negative for any growth.

TABLE XIII

| Filter # | Number of Spores Injected Total | Renalin ® Used, ml | Dwell Time, hours | Incubation Period, hours | Post-Treatment Spores Viable, cfu/ml |
|---|---|---|---|---|---|
| 1 | 100 Billion | 25 | 12 | 48 | 0 |
| 2 | 100 Billion | 20 | 6 | 72 | 0 |
| 3 | 100 Billion | 10 | 6.5 | 48 | 0 |
| 4 | 100 Billion | 10 | 6 | 48 | 0 |

Example 24

A filter as described in Example 8 was challanged by exposing it to three back-to-back 85° C. heat disinfection treatments using a Fresenius A2008H dialysis machine. The filter's endotoxin retention capability was evaluated after exposure.

A dialysate filter was installed on a Fresenius A2008H dialysis machine between the dialyzer-in and dialyzer-out dialysate lines. The dialysis machine was turned on and the heat disinfection cycle was initiated. Upon completion of this cycle, it was immediately re-initiated two more times.

After completing all three cycles, the filter was removed from the machine and installed on a test bench for delivering an endotoxin challenge into the filter's inlet stream.

DI water throughput was initiated at 500 ml/min and continued for the duration of the test. Endotoxin derived from Escherichia coli was introduced into the filter's inlet stream at 15.4 EU/ml. Filtrate endotoxin levels were measured using the gel-clot method of Limulus Amebocyte Lysate endotoxin assaying.

Filter inlet and outlet pressures were also measured and compared to values recorded prior to heat treatments.

With 500 ml/min DI water throughput, containing a 15.4 EU/ml Escherichia coli endotoxin level, no endotoxin was detected in filter outlet samples at 1, 3, and 5 minutes. No detectable endotoxin was recorded as <0.06 EU/ml, the limit of lysate sensitivity to the presence of endotoxin. The pressure drop across the filter did not change from values recorded prior to heat treatment exposures.

Example 25

Filters as described in Example 8 were exposed to exaggerated bleach contact conditions using a COBE Centry 2Rx or Travenol 450 SPS dialysis machine. The filters were re-evaluated for endotoxin retention capability after exposure.

Three filters were exposed to full-strength bleach (5.25% sodium hypochlorite) during 600 ml/min throughput of either RO water, acetate dialysate, or final bicarbonate-based dialysate solutions using a Travenol 450 SPS dialysis machine. Eight injections of undiluted bleach, 20 cc each, were delivered into the inlet stream of each filter at 15 minute intervals.

Two filters were exposed to approximately 30 days' worth of bleach treatments. Both filters were given six exposures of 1,250 ml each, with a 5 minute rinse between each exposure. The dilution level was 1:8 bleach in RO water. The dilution was accomplished by using a COBE Centry 2Rx dialysis machine. The total bleach contact time was 2 hours and 5 minutes. The filters were installed on the dialysis machine and the bleaching procedure followed right out of the COBE Centry 2Rx Operator's manual. The only exception was that 7,500 ml of bleach was used instead of the 250 ml specified in the procedure.

All five filters were rinsed with DI water on the dialysis machine until 0 ppm of free chlorine was detected using Hach Co. "powder pillows" for chlorine testing and the color comparator wheel provided with the test kit.

Filters were then installed on a test bench for administering the endotoxin challenge, identical to the one used in Example 24.

DI water throughput was initiated at 500 ml/min and continued for the duration of the test. Endotoxin derived from Escherichia [coil] *coli* was introduced into the filter's inlet stream at ≧3.8 EU/ml. Filtrate endotoxin levels were measured using the gel-clot method of Limulus Amebocyte Lysate endotoxin assaying.

Filter inlet and outlet pressures were also measured and compared to values recorded prior to bleach treatments.

Note that in this Example (Table), results of no detectable endotoxin are recorded as <0.06 EU/ml, the limit of lysate sensitivity for the test.

The first filter, exposed to bicarbonate dialysate throughput and eight 20 cc bleach injections, was challenged with ≧7.7 EU/ml level of Escherichia coli endotoxin. No endotoxin was detected in filter outlet samples at 5, 30, and 60 minutes.

The second filter, exposed to acetate dialysate throughput and eight 20 cc bleach injections, was challenged with ≧7.7 EU/ml level of Escherichia coli endotoxin. No endotoxin was detected in filter outlet samples at 5, 30, and 60 minutes.

The third filter, exposed to RO water throughput and eight 20 cc bleach injections, was challenged with ≧7.7 EU/ml level of Escherichia coli endotoxin. No endotoxin was detected in filter outlet samples at 5, 30, and 60 minutes.

The fourth filter, exposed to 30 days' worth of bleach treatments, was challenged with ≧3.8 EU/ml level of Escherichia coli endotoxin. No endotoxin was detected in filter outlet samples at 1, 3, and 5 minutes.

The fifth filter, exposed to 30 days' worth of bleach treatments, was challenged with ≧15.4 EU/ml level of Escherichia coli endotoxin. No endotoxin was detected in filter outlet samples at 1, 3, and 5 minutes.

The transmembrane pressure drop across all filters decreased by one-half after bleach exposure. This parallels the normal TMP drop seen when other dialysate filters have been exposed to dialysate the first time.

TABLE XIV

| Filter # | Pre-treat Conditions | Endotoxin Challenge Level | Filtrate Endoroxin Level |
|---|---|---|---|
| 1 | Eight injections of 20 cc bleach delivered during bicarbonate throughput | 7.7 EU/ml | <0.06 EU/ml |
| 2 | Eight injections of 20 cc bleach delivered during bicarbonate throughput | 7.7 EU/ml | <0.06 EU/ml |
| 3 | Eight injections of 20 cc bleach delivered during RO water throughput | 7.7 EU/ml | <0.06 EU/ml |
| 4 | 30 Days' worth of bleach treatments | 3.8 EU/ml | <0.06 EU/ml |

TABLE XIV-continued

| Filter # | Pre-treat Conditions | Endotoxin Challenge Level | Filtrate Endoroxin Level |
|---|---|---|---|
| 5 | 30 Days' worth of bleach treatments | 15.4 EU/ml | <0.06 EU/ml |

Example 26

A filter as described in Example 8 was exposed to 30 days' worth of Actril® disinfection treatments using a Travenol 450 SPS dialysis machine. The filters' endotoxin retention capability after exposure was reevaluated.

One filter was exposed to approximately 30 days' worth of Actril® treatments. The filter was given six exposures of 1,250 ml each, with a 5 minute rinse between each exposure. The dilution level was 1:8 Actril® in RO water. The dilution was accomplished by using a COBE Centry 2Rx dialysis machine. The total Actril® contact time was 2 hours and 5 minutes. The filter was installed on the dialysis machine and the procedure followed right out of the COBE Centry 2Rx Operator's manual. The only exceptions were that 7,500 ml of chemical was used instead of the 250 ml specified in the procedure, and, Actril® was used instead of bleach.

The filter was rinsed with DI water on the dialysis machine until <1 ppm of hydrogen peroxide was detected using Renalin® residual test strips (for hydrogen peroxide, not peracetic acid).

The filters was then installed on a test bench for administering the endotoxin challenge, identical to the one used in Example 24.

DI water throughput was initiated at 500 ml/min and continued for the duration of the test. Endotoxin derived from Escherichia coli was introduced into the filter's inlet stream at ≧15.4 EU/ml. Filtrate endotoxin levels were measured using the gel-clot method of Limulus Amebocyte Lysate endotoxin assaying.

Filter inlet and outlet pressures were also measured and compared to values recorded prior to bleach treatments.

With 500 ml/min DI water throughput, containing a 15.4 EU/ml Escherichia coli endotoxin level, no endotoxin was detected in filter outlet samples at 1, 3, and 5 minutes. No detectable endotoxin is recorded as <0.06 EU/ml, the limit of lysate sensitivity to the presence of endotoxin. The pressure drop across the filter did not change from values recorded prior to Actril® treatment exposures.

Example 27

A filter as described in Example 8 was exposed to Renalin® contact conditions using a Travenol 450 SPS dialysis machine. The filter's endotoxin retention capability after exposure was reevaluated.

Four dialysate filters that had been exposed to conditions which caused them to release LAL-reactive material into throughput solutions, were treated with a 250 ml 1:8 dilution Renalin® in RO water solution and reverse flow conditions. Renalin® residuals were rinsed to <1 ppm hydrogen peroxide. Endotoxin retention capability was re-evaluated after rinsing has been completed.

To produce this condition in which filters release or "shed" LAL-reactive material, filters were run 24 hours/day at 800 ml/min on a recirculation setup with contaminated dialysate. NOTE: Shedding only occurs in filters that have not been periodically re-sterilized during use (every 24–48 hours).

It was observed, that at a point between 10,000 liters and 20,000 liters total dialysate throughput, the filters began "shedding" LAL-reactive material into the filtrate.

Before the re-evaluation of endotoxin retention was conducted, all four units were pre-treated on the "recirculation" setup until they began to "shed" LAL-reactive material into throughput solutions. "Shedding" was verified using gel-clot LAL assays of filtrate samples.

Once "shedding" was verified, all four units were exposed to a Renalin Concentrate disinfection treatment.

The Renalin® membrane disinfection and clearing procedure consisted of the following steps:

a. Removing the filter from the recirculating setup.
b. Installing it in reverse configuration (to "blow off" the material impacted on the membrane surface) on a Travenol 450 SPS dialysis machine, in between the dialysate in-flow and out-flow lines.
c. Running RO water through the filter at 600 ml/min during a Renalin® Concentrate chemical treatment on the dialysis machine.
   1) Allowing the dialysis machine to draw up 250 ml of Renalin® Concentrate through the acid concentrate uptake line (resulting in a 1:8 dilution of Renalin® Concentrate in the filter and machine dialysate lines).
   2) Turning off the dialysis machine and allowing the diluted Renalin® Concentrate to dwell inside the filter for 30 minutes.
   3) Turning on the dialysis machine and "rinsing" the filter with RO water until <1 ppm of Renalin® was detected. This took about 20 minutes to accomplish.
d. Re-orienting the filter to normal flow direction and installing it on the endotoxin challenge test bench.

After the Renalin® treatment, all four filters were installed one-at-a-time on the endotoxin challenge test bench in preparation for the post-treatment LPS retention test.

This endotoxin test setup consisted of a roller pump, inlet and outlet tubing and Hansen-style connectors, pre- and postfilter sampling ports, and 2½ gallon polyethylene containers for holding the challenge solutions. All tests used DI water throughput at a flowrate=500 ml/min.

Again, the gel-clot method of Limulus Amebocyte Lysate endotoxin assaying was used to analyze all samples for presence, absence, or quantification of endotoxin.

Frozen, dried lipopolysaccharide (LPS, endotoxin), isolated from Escherichia coli by phenol extraction, was reconstituted per the manufacturer's instructions and added to a 2½ gallon container of pyrogen-free RO water immediately prior to initiating the test. The 2½ gallon container was vigorously shaken and then placed on a magnetic stirring platform, with a stirring bar in the bottom, to help keep the solution mixed.

Once the LPS contamination was initiated, samples were collected from filter inlet and outlet sample ports at T=1, 3, and 5 minutes.

Filters subjected to a Renalin® membrane clearing and disinfecting procedure and receiving follow-up endotoxin challenges varying in potency had the following [resutls,] *results* with a challenge from ≧7.7 EU/ml up to 30.7 EU/ml of Escherichia coli endotoxin in RO water at throughput flowrates of 500 ml/min, each filter retained all endotoxin contained within the challenge solution. No detectable endotoxin is reported as <0.06 EU/ml, the limit of sensitivity for the Lysate used in the assay. (See Table below for details.)

TABLE XV

Recovery of Endotoxin Retention After Renalin ® Exposure

| Filter # | Treatment conditions | "Shedding" LAL-reactive Material before Renalin ® Treatment ? (Y/N) | Endotoxin Challenge Level, EU/Ml (After Renalin ®) | Endotoxin Filtrate Level, EU/ml 1 MIN | 3 MIN | 5 MIN |
|---|---|---|---|---|---|---|
| 1 | 20,000 liters recirculated dialysate, then Renalin ®-treated | Yes, >0.06 EU/ml | 15.4 | <0.06 | <0.06 | <0.06 |
| 2 | 20,000 liters recirculated dialysate, then Renalin ®-treated | Yes, >0.06 EU/ml | 15.4 | <0.06 | <0.06 | <0.06 |
| 3 | 20,000 liters recirculated dialysate, then Renalin ®-treated | Yes, >0.06 EU/ml | 7.7 | <0.06 | <0.06 | <0.06 |
| 4 | 20,000 liters recirculated dialysate, then Renalin ®-treated | Yes, >0.06 EU/ml | 30.7 | <0.06 | <0.06 | <0.06 |

Example 28

A filter as described in Example 8 was exposed to an amount of bleach contact consistent with normal dialysis machine "low-level" disinfection, and, a clearance curve (ppm vs. time) of residual free chlorine levels during 500 ml/min RO water throughput was plotted.

A dialysate filter was installed on a COBE Centry 2 Rx dialysis machine, and a bleach treatment was performed as described in the COBE Centry 2Rx Operator's Handbook.

This treatment consisted of an exposure to a 1:8 dilution bleach (0.65% sodium hypochlorite) in water solution while the filter was installed on the dialysis machine.

At the end of the bleach treatment, samples of the filter's outlet fluid were collected about every minute for 15 minutes.

These samples were analyzed using a Beckman DU-640 Spectrophotometer which had been calibrated to analyze free chlorine levels in samples tested.

These results were plotted on a time vs. ppm free chlorine concentration and the time required to rinse free chlorine to levels <1 ppm was noted.

Free chlorine residuals rinsed from the filter down to 1.6 ppm within 10 minutes at a 470 ml/min RO water throughput flow rate.

Example 29

A filter as described in Example 8 was exposed to an amount of Actril® contact consistent with normal dialysis machine "low-level" disinfection, and, a clearance curve (ppm vs. time) of residual hydrogen peroxide levels during 500 ml/min RO water throughput was plotted.

A dialysate filter was installed on a COBE Centry 2 Rx dialysis machine, and a chemical treatment was performed as described in the COBE Centry 2Rx Operator's Handbook, substituting Actril® for bleach as the chemical used.

This treatment consisted of an exposure to a 1:8 dilution Actril® (0.1% hydrogen peroxide) in water solution while the filter was installed on the dialysis machine.

At the end of the Actril® treatment, samples of the filter's outlet fluid were collected about every minute for 15 minutes.

These samples were analyzed using a Beckman DU-640 Spectrophotometer which had been calibrated to analyze hydrogen peroxide levels in samples tested.

These results were plotted on a time vs. ppm hydrogen peroxide concentration and the time required to rinse hydrogen peroxide to levels <1 ppm was noted.

Hydrogen peroxide residuals rinsed from the filter down to 0.6 ppm within 10 minutes at a 470 ml/min RO water throughput flow rate.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. A filter comprising;

a housing defining an interior chamber;

an inlet port connected to said housing;

an outlet port connected to said housing;

an access port connected to said housing; and a bundle of asymmetric, microporous, hollow fiber membranes disposed within said interior chamber, said asymmetric, microporous, hollow fiber membranes comprising a polyimide polymer, said asymmetric, microporous, hollow fiber membranes including pores having a pore size range from about 0.005 $\mu$m to about 0.2 $\mu$m, wherein said asymmetric, microporous, hollow fiber membranes have a flux in excess of about $75\times10^{-5}$ ml/(min×cm$^2$×mmHg); and wherein said inlet port, said outlet port and said access port are in fluid communication with said bundle of hollow fiber membranes.

2. The filter of claim 1 wherein said fiber comprises 100 wt. % of said polyimide polymer.

3. The filter of claim [2] *1* wherein said polyimide polymer comprises a polymer having the structure:

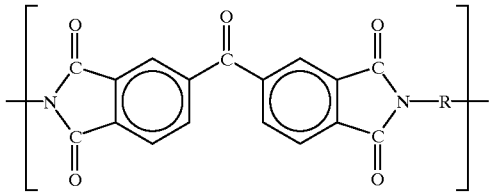

10% to 90% of the R groups are

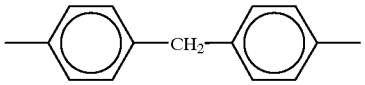

and the remaining R groups are

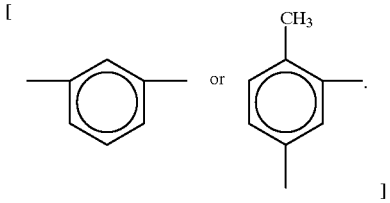

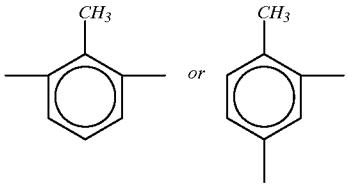

4. The filter of claim 3 wherein said fiber comprises from about 100 wt. % of said polyimide polymer.

5. The filter of claim 1 wherein said polyimide polymer comprises a polymer having the structure:

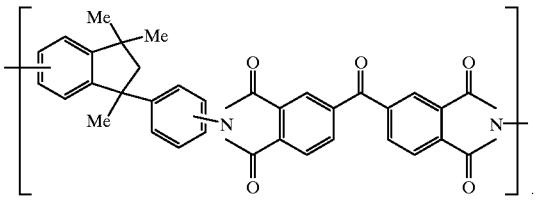

6. The filter of claim 5 wherein said [fiber] *polyimide polymer* comprises from about 100 wt. % of said polyimide polymer.

7. The filter of claim 2 wherein said polyimide polymer comprises a polymer having the structure:

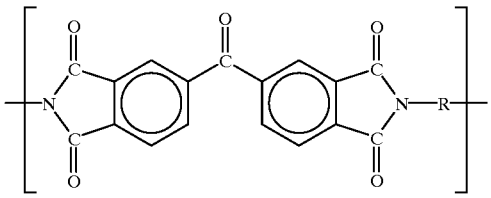

wherein 10% to 90% of the R groups are

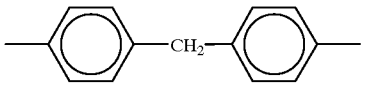

and the remaining R groups are

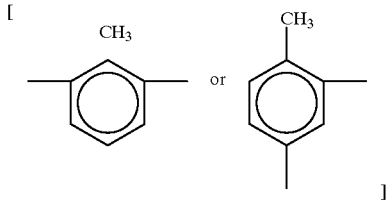

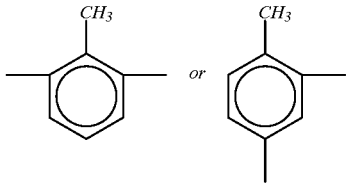

8. [The filter of claim 7 wherein said polyimide polymer comprises from about 100 wt. % of said polyimide polymer.] *The filter of claim 2 wherein said polyimide polymer comprises a polymer having the structure:*

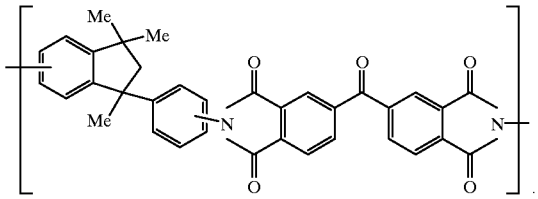

9. The filter of claim 1 wherein said polyimide polymer has a molecular weight of about 40,000 daltons to about 105,000 daltons.

10. The filter of claim 1 wherein said membranes are uniformly porous throughout and wherein said membranes are characterized by the absence of voids.

11. The filter of claim 1 wherein said membranes are capable of being subjected to take-up rates in excess of 45 m/min during manufacturing.

12. The filter of claim 1 wherein said membranes rewet by maintaining a flux of at least 500 ml/(hr×m$^2$×mmHg) for six or more sterilizations and wherein said asymmetric, microporous, hollow fiber membranes are further characterized by having 0.0% wetting agent additives selected from the group of hydrophilic polymers, nonionic, anionic, or amphoteric surfactants.

13. The filter of claim 12 wherein said hydrophilic polymers comprise polyvinylpyrrolidone.

14. The filter of claim 1 wherein the housing is a material selected from polycarbonate, polyethylene or polypropylene.

15. The filter of claim 1 wherein the housing is polycarbonate.

16. A dialysis apparatus comprising:

a dialysis system comprising an artificial kidney operatively connected to said dialysis system, said artificial kidney including a dialysate inlet port;

a female to female connector; and a dialysate filter, said dialysate filter comprising:

a bundle of asymmetric, microporous, hollow fiber membranes;

a filter housing defining an interior chamber;

a dialysate inlet port connected to said filter housing;

a dialysate outlet port connected to said filter housing;

a dialysate access port connected to said filter housing;

and said bundle of asymmetric, microporous, hollow fiber membranes disposed within said interior chamber, said asymmetric microporous hollow fiber membranes comprising a polyimide polymer, said asymmetric, microporous, hollow fiber membranes including pores having a pore size range from about 0.005 $\mu$m to about 0.2 $\mu$m, and having a flux in excess of about $75\times10^{-5}$ ml/(min×cm$^2$×mmHg); said dialysate inlet port, said dialysate outlet port and said access port are in fluid communication with said bundle of hollow fiber membranes; and wherein the dialysate filter is located upstream of the artificial kidney and is connected through the female to female connector to the inlet port of said artificial kidney.

17. The dialysis apparatus of claim 16 wherein said filter is connected directly to said female to female connector at the dialysate inlet port of said artificial kidney.

18. [A] *The* dialysis apparatus [comprising] of claim 16 wherein said filter is connected to said female to female connector by a hose.

19. The dialysis apparatus of claim 16 wherein said fiber comprises 100 wt. % of said polyimide polymer.

20. The filter of claim 16 wherein said polyimide polymer comprises a polymer having the structure:

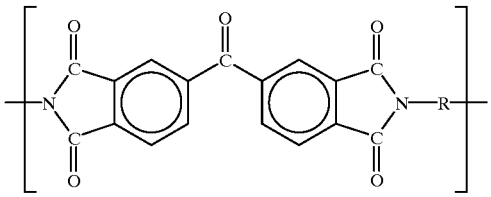

wherein 10% to 90% of the R groups are

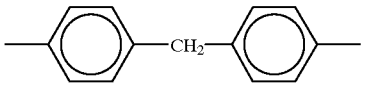

and the remaining R groups are

[

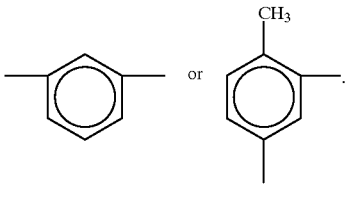

]

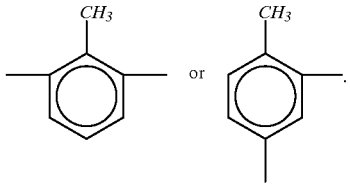

21. The dialysis apparatus of claim 20 wherein said fiber comprises from about 100 wt. % of said polyimide polymer.

22. The dialysis apparatus of claim 16 wherein said polyimide polymer comprises a polymer having the structure:

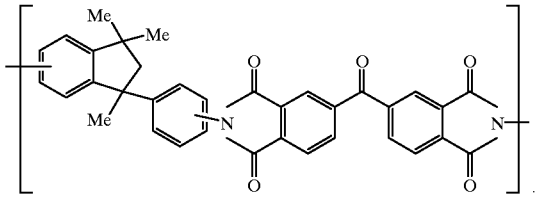

23. The dialysis apparatus of claim 22 wherein said polyimide polymer comprises from about 100 wt. % of said polyimide polymer.

24. The dialysis apparatus of claim 16 wherein said polyimide polymer has a molecular weight of about 40,000 daltons to about 105,000 daltons.

25. The dialysis apparatus of claim 16 wherein said membranes are uniformly porous throughout and wherein said membranes are characterized by the absence of voids.

26. The dialysis apparatus of claim 16 wherein said membranes are capable of being subjected to take-up rates in excess of 45 m/min during manufacturing.

27. The filter of claim 16 wherein said membranes rewet by maintaining a flux of at least 500 ml/(hr×m$^2$×mmHg) for six or more sterilizations and wherein said asymmetric, microporous, hollow fiber membranes are further characterized by having 0.0% wetting agent additives selected from the group of hydrophilic polymers, nonionic, anionic, or amphoteric surfactants.

28. The dialysis apparatus of claim 27 wherein said hydrophilic polymers comprise polyvinylpyrolidone.

29. The dialysis apparatus of claim 16 wherein the housing is a material selected from polycarbonate, polyethylene or polypropylene.

30. The dialysis apparatus of claim 16 wherein the housing is polycarbonate.

* * * * *

UNITED STATES PATENT AND TRADEMARK OFFICE

CERTIFICATE OF CORRECTION

PATENT NO. : RE 36,914
DATED : October 17, 2000
INVENTOR(S) : Daniel B. Carlsen et al.

It is certified that error appears in the above-identified patent and that said Letters Patent is hereby corrected as shown below:

Title page,
Insert the following below item [76]:

-- [73] Assignee: Minntech Corporation, Minneapolis, MN --.

Signed and Sealed this

Ninth Day of December, 2003

JAMES E. ROGAN
*Director of the United States Patent and Trademark Office*